(12) United States Patent
Dutkiewicz et al.

(10) Patent No.: US 8,946,100 B2
(45) Date of Patent: Feb. 3, 2015

(54) FIBERS OF VARIABLE WETTABILITY AND MATERIALS CONTAINING THE FIBERS

(75) Inventors: Jacek K. Dutkiewicz, Cordova, TN (US); Stephen A. Skirius, Collierville, TN (US); Sonja McNeil Fields, Memphis, TN (US); Lynn Hung Rushing, Olive Branch, MS (US); David Jay Smith, Germantown, TN (US); Michael Kalmon, Boyertown, PA (US); Ronald Timothy Moose, Lakeland, TN (US); Ryszard Fryczkowski, Bielsko-Biala (PL); Beata Fryczkowska, Bielsko-Biala (PL); Monika Rom, Bielsko-Biala (PL)

(73) Assignee: Buckeye Technologies Inc., Memphis, TN (US)

( * ) Notice: Subject to any disclaimer, the term of this patent is extended or adjusted under 35 U.S.C. 154(b) by 1534 days.

(21) Appl. No.: 11/471,040

(22) Filed: Jun. 19, 2006

(65) Prior Publication Data
US 2006/0292951 A1    Dec. 28, 2006

Related U.S. Application Data

(63) Continuation of application No. PCT/US2004/043030, filed on Dec. 20, 2004.

(60) Provisional application No. 60/531,706, filed on Dec. 19, 2003, provisional application No. 60/569,980, filed on May 10, 2004.

(51) Int. Cl.
*B32B 5/02* (2006.01)
*A61L 15/52* (2006.01)
(Continued)

(52) U.S. Cl.
CPC .......... *A61L 15/52* (2013.01); *A61F 13/53747* (2013.01); *D06M 11/00* (2013.01);
(Continued)

(58) Field of Classification Search
USPC ......... 428/342; 442/79, 85, 86; 604/381, 358, 604/367, 370, 371, 374, 375, 378
See application file for complete search history.

(56) References Cited

U.S. PATENT DOCUMENTS

| 213,100 | A |   | 3/1879 | Eaton |   |
|---|---|---|---|---|---|
| 1,536,254 | A | * | 5/1925 | White | ............................. 442/79 |

(Continued)

FOREIGN PATENT DOCUMENTS

| CA | 1193808 | 9/1985 |
|---|---|---|
| EP | 463388 | 1/1992 |

(Continued)

OTHER PUBLICATIONS

U.S. Appl. No. 09/774,248, filed Jan. 30, 2001, Gross et al.
(Continued)

*Primary Examiner* — Matthew Matzek
(74) *Attorney, Agent, or Firm* — Baker Botts LLP

(57) ABSTRACT

The present invention is directed to an absorbent material and the fibers therein, having two or more layers including an upper surface layer which has on the outer surface of the layer one or more surface area zones which are more wettable zones and adjacent thereto one or more less wettable zones, where the more wettable zones have a greater hydrophilicity than the less wettable zone. The present invention is also directed to the fibers therein, which contain polyvalent cation-containing compounds and fatty acid containing compounds. The present invention also provides for methods of treating fibers or solid materials and processes of producing the hydrophobic materials.

10 Claims, 10 Drawing Sheets

(51) Int. Cl.
*A61F 13/537* (2006.01)
*D06M 11/00* (2006.01)
*D06M 11/57* (2006.01)
*D06M 13/184* (2006.01)
*D06M 13/188* (2006.01)
*D06M 13/224* (2006.01)
*D06M 23/06* (2006.01)
*D21C 9/00* (2006.01)
*D21H 21/22* (2006.01)
*D21H 17/14* (2006.01)
*D21H 27/30* (2006.01)

(52) U.S. Cl.
CPC ............ *D06M 11/57* (2013.01); *D06M 13/184* (2013.01); *D06M 13/188* (2013.01); *D06M 13/224* (2013.01); *D06M 23/06* (2013.01); *D21C 9/002* (2013.01); *D21H 21/22* (2013.01); *D06M 2200/12* (2013.01); *D21H 17/14* (2013.01); *D21H 27/30* (2013.01)
USPC .................................. 442/79; 442/85; 442/86

(56) References Cited

U.S. PATENT DOCUMENTS

| | | | | |
|---|---|---|---|---|
| 1,571,048 | A | 1/1926 | Garrow | |
| 1,990,292 | A | 2/1935 | Leatherman | |
| 2,032,645 | A | 3/1936 | Youtz | |
| 2,097,589 | A | 11/1937 | Dreyfus | |
| 2,289,282 | A | 7/1942 | Brodersen et al. | |
| 2,525,049 | A | 10/1950 | Signaigo | |
| 2,686,121 | A * | 8/1954 | Latham et al. | 162/165 |
| 2,739,871 | A | 3/1956 | Senkus et al. | |
| 2,983,722 | A | 5/1961 | Horowitz et al. | |
| 3,053,607 | A | 9/1962 | Gulledge | |
| 3,224,926 | A | 12/1965 | Bernardin | |
| 3,241,553 | A | 3/1966 | Steiger | |
| 3,693,622 | A * | 9/1972 | Jones, Sr. | 604/375 |
| 3,756,913 | A | 9/1973 | Wodka | |
| 3,873,354 | A | 3/1975 | Walters | |
| 3,901,238 | A | 8/1975 | Gellert et al. | |
| 3,932,209 | A | 1/1976 | Chatterjee | |
| 3,935,363 | A | 1/1976 | Burkholder et al. | |
| 3,998,690 | A | 12/1976 | Lyness et al. | |
| 4,035,147 | A | 7/1977 | Sangenis et al. | |
| 4,043,952 | A | 8/1977 | Ganslaw et al. | |
| 4,084,033 | A * | 4/1978 | Drelich | 428/198 |
| 4,090,013 | A | 5/1978 | Ganslaw et al. | |
| 4,102,340 | A | 7/1978 | Mesek et al. | |
| 4,214,582 | A | 7/1980 | Patel | |
| 4,295,987 | A | 10/1981 | Parks | |
| 4,302,369 | A | 11/1981 | Elmquist | |
| 4,306,911 | A | 12/1981 | Gordon et al. | |
| 4,406,703 | A | 9/1983 | Guthrie et al. | |
| 4,447,570 | A * | 5/1984 | Cook et al. | 524/127 |
| 4,467,012 | A | 8/1984 | Pedersen et al. | |
| 4,469,746 | A | 9/1984 | Weisman et al. | |
| 4,506,684 | A | 3/1985 | Keritsis | |
| 4,548,847 | A | 10/1985 | Aberson et al. | |
| 4,558,091 | A | 12/1985 | Hubbard | |
| 4,689,118 | A | 8/1987 | Makoui et al. | |
| 4,699,823 | A | 10/1987 | Kellenberger et al. | |
| 4,715,931 | A | 12/1987 | Schellhamer et al. | |
| RE32,649 | E | 4/1988 | Brandt et al. | |
| 4,822,453 | A * | 4/1989 | Dean et al. | 162/157.6 |
| 4,838,885 | A | 6/1989 | Bernardin | |
| 4,888,238 | A | 12/1989 | Katz et al. | |
| 4,898,642 | A | 2/1990 | Moore et al. | |
| 4,919,681 | A | 4/1990 | Tyler et al. | |
| 4,935,022 | A | 6/1990 | Lash et al. | |
| 4,950,264 | A | 8/1990 | Osborn, III | |
| 4,950,265 | A | 8/1990 | Taylor | |
| 4,952,550 | A | 8/1990 | Wallach et al. | |
| 5,068,079 | A | 11/1991 | Gustafsson | |
| 5,137,537 | A | 8/1992 | Herron et al. | |
| 5,147,343 | A | 9/1992 | Kellenberger | |
| 5,149,335 | A | 9/1992 | Kellenberger et al. | |
| 5,183,707 | A | 2/1993 | Herron et al. | |
| 5,190,563 | A | 3/1993 | Herron et al. | |
| 5,217,445 | A | 6/1993 | Young et al. | |
| 5,269,049 | A | 12/1993 | Gustafsson | |
| 5,294,299 | A | 3/1994 | Zeuner et al. | |
| 5,300,192 | A | 4/1994 | Hansen et al. | |
| 5,328,935 | A | 7/1994 | Van Phan et al. | |
| 5,338,766 | A | 8/1994 | Phan et al. | |
| 5,350,799 | A | 9/1994 | Woodrum et al. | |
| 5,360,420 | A | 11/1994 | Cook et al. | |
| 5,372,766 | A | 12/1994 | Roe | |
| 5,399,591 | A | 3/1995 | Smith et al. | |
| 5,413,676 | A | 5/1995 | Nguyen et al. | |
| 5,417,977 | A | 5/1995 | Honeycutt | |
| 5,427,844 | A | 6/1995 | Murai et al. | |
| 5,432,000 | A | 7/1995 | Young, Sr. et al. | |
| 5,451,613 | A | 9/1995 | Smith et al. | |
| 5,462,972 | A | 10/1995 | Smith et al. | |
| 5,484,896 | A | 1/1996 | Naieni et al. | |
| 5,489,469 | A | 2/1996 | Kobayashi et al. | |
| 5,492,759 | A | 2/1996 | Eriksson et al. | |
| 5,562,642 | A | 10/1996 | Smith et al. | |
| 5,562,646 | A | 10/1996 | Goldman et al. | |
| 5,589,256 | A | 12/1996 | Hansen et al. | |
| 5,601,921 | A | 2/1997 | Eriksson | |
| 5,611,890 | A | 3/1997 | Vinson et al. | |
| 5,635,191 | A * | 6/1997 | Roe et al. | 424/402 |
| 5,693,162 | A | 12/1997 | Gustafsson | |
| 5,695,486 | A | 12/1997 | Broughton | |
| 5,721,295 | A | 2/1998 | Bruggemann et al. | |
| 5,736,595 | A | 4/1998 | Gunther et al. | |
| 5,773,542 | A | 6/1998 | Koudate et al. | |
| 5,789,326 | A | 8/1998 | Hansen et al. | |
| 5,795,439 | A | 8/1998 | Euripides et al. | |
| 5,795,515 | A | 8/1998 | Fischer | |
| 5,847,031 | A | 12/1998 | Klimmek et al. | |
| 5,849,816 | A | 12/1998 | Suskind et al. | |
| 5,858,021 | A | 1/1999 | Sun et al. | |
| 5,859,077 | A | 1/1999 | Reichman et al. | |
| 5,922,163 | A | 7/1999 | Helynranta | |
| 5,961,505 | A | 10/1999 | Coe et al. | |
| 5,998,695 | A | 12/1999 | Roe et al. | |
| 6,007,653 | A | 12/1999 | Pirinen et al. | |
| 6,040,251 | A | 3/2000 | Caldwell | |
| 6,074,530 | A | 6/2000 | Tillirson | |
| 6,080,277 | A | 6/2000 | Oberkofler et al. | |
| 6,099,950 | A | 8/2000 | Wang et al. | |
| 6,127,593 | A | 10/2000 | Bjorkquist et al. | |
| 6,139,941 | A | 10/2000 | Jankevics et al. | |
| 6,159,335 | A | 12/2000 | Owens et al. | |
| 6,171,441 | B1 | 1/2001 | Phillips et al. | |
| 6,183,847 | B1 | 2/2001 | Goldwasser | |
| 6,222,091 | B1 | 4/2001 | Beihoffer et al. | |
| 6,228,217 | B1 | 5/2001 | Dickerson et al. | |
| 6,235,965 | B1 | 5/2001 | Beihoffer et al. | |
| 6,241,713 | B1 | 6/2001 | Gross et al. | |
| 6,296,737 | B1 | 10/2001 | Wu et al. | |
| 6,340,408 | B1 | 1/2002 | Norlander | |
| 6,342,268 | B1 | 1/2002 | Samain | |
| 6,344,109 | B1 | 2/2002 | Gross | |
| 6,353,148 | B1 | 3/2002 | Gross | |
| 6,355,079 | B1 | 3/2002 | Sorvari et al. | |
| 6,403,857 | B1 | 6/2002 | Gross et al. | |
| 6,420,626 | B1 | 7/2002 | Erspamer et al. | |
| 6,433,058 | B1 | 8/2002 | Weir et al. | |
| 6,479,415 | B1 | 11/2002 | Baer et al. | |
| 6,495,734 | B1 | 12/2002 | Fields et al. | |
| 6,559,081 | B1 | 5/2003 | Erspamer et al. | |
| 6,562,742 | B2 | 5/2003 | Dutkiewicz et al. | |
| 6,562,743 | B1 * | 5/2003 | Cook et al. | 442/409 |
| 6,770,576 | B2 | 8/2004 | Cook et al. | |
| 8,097,767 | B2 | 1/2012 | Catalan | |
| 8,101,814 | B2 | 1/2012 | Mirle et al. | |
| 2002/0013560 | A1 | 1/2002 | Erspamer et al. | |

(56) References Cited

U.S. PATENT DOCUMENTS

| | | |
|---|---|---|
| 2003/0093045 A1 | 5/2003 | Erdman |
| 2004/0224588 A1 | 11/2004 | Cook et al. |
| 2004/0241216 A1* | 12/2004 | Klun et al. .................. 424/445 |

FOREIGN PATENT DOCUMENTS

| | | |
|---|---|---|
| EP | 644207 | 3/1995 |
| EP | 733648 | 9/1996 |
| EP | 856528 | 8/1998 |
| EP | 889063 | 7/1999 |
| GB | 469037 | 7/1937 |
| JP | 7228788 | 8/1995 |
| JP | 9176427 | 7/1997 |
| SE | 462918 | 9/1990 |
| WO | WO9739188 | 10/1997 |
| WO | WO9817856 | 4/1998 |
| WO | WO9955393 | 11/1999 |
| WO | WO9955767 | 11/1999 |
| WO | WO 00/38607 | 7/2000 |
| WO | WO 01/87215 | 11/2001 |
| WO | WO 03/039852 | 5/2003 |
| WO | WO 2005/063309 | 7/2005 |

OTHER PUBLICATIONS

U.S. Appl. No. 60/531,706, filed Dec. 19, 2003, Dutkiewicz et al.
U.S. Appl. No. 60/569,980, filed Oct. 5, 2004, Dutkiewicz et al.
Dutkiewicz, J. Nonwoven Structures for Absorption of Body Fluids (sub-chapter 2.1). Basic Structural Properties of Absorbent Networks. Edana, Belgium (2003): 7-20.
Dutkiewicz, Jacek. Some Advances in Nonwoven Structures for Absorbency, Comfort and Aesthetics. AUTEX Research Journal, vol. 2, No. 3, Sep. 2002. Buckeye Technologies Inc. pp. 153-165.
Buchholz, F. et al., Modern Superabsorbent Polymer Technology, pp. 56-58.
J. Grignon et al., "Effect of pH and Neutral Salts upon the Swelling of Cellulose Gels", Journal of Applied Polymer Science, vol. 125, 2829-2843 (1980).
U.S. Appl. No. 10/360,147, filed Apr. 14, 2004, Notice of Allowance.
U.S. Appl. No. 10/360,147, filed Feb. 4, 2004, Supplemental Response/Amendment.
U.S. Appl. No. 10/360,147, filed Jan. 29, 2004, Response to Non-Final Rejection.
U.S. Appl. No. 10/360,147, filed Nov. 20, 2003, Non-Final Rejection.
U.S. Appl. No. 10/866,210, filed Jan. 31, 2008, Final Rejection.
U.S. Appl. No. 10/866,210, filed Nov. 14, 2007, Response to Non-Final Rejection.
U.S. Appl. No. 10/866,210, filed Aug. 23, 2007, Non-Final Rejection.
U.S. Appl. No. 10/866,210, filed Jun. 18, 2007, Response to Final Rejection and RCE filed.
U.S. Appl. No. 10/866,210, filed Dec. 18, 2006, Non-Final Rejection.
U.S. Appl. No. 10/866,210, filed Oct. 30, 2006, Resposne to Non-Final Rejection.
U.S. Appl. No. 10/866,210, filed Jun. 28, 2006, Non-Final Rejection.

* cited by examiner

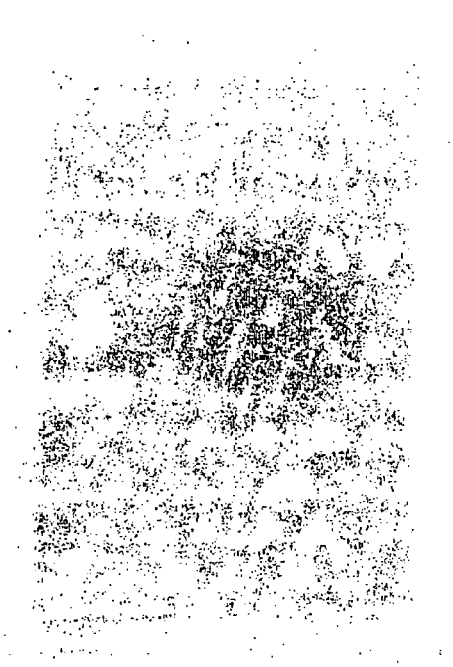 
Figure 3A                    Figure 3B

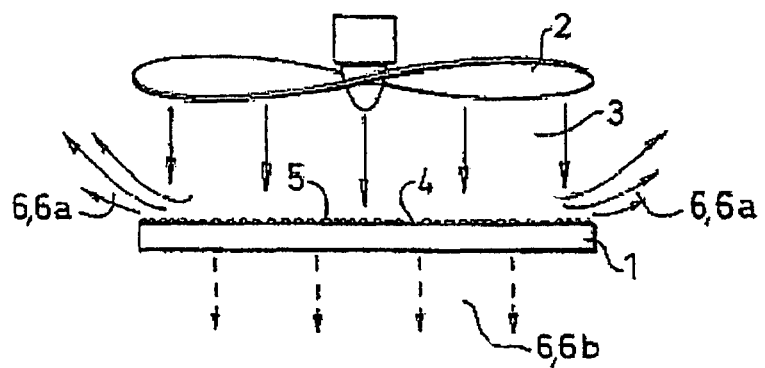
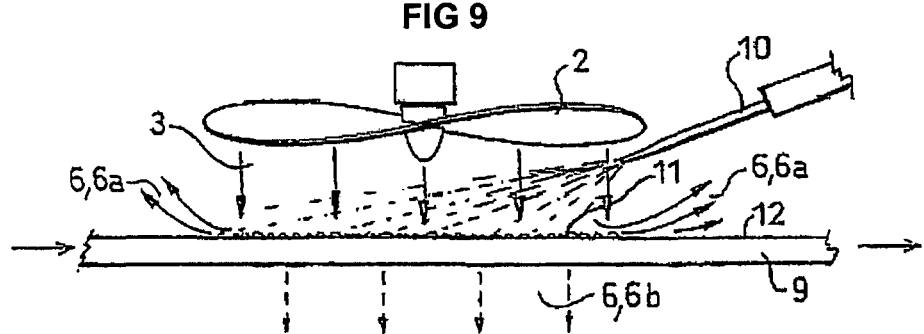

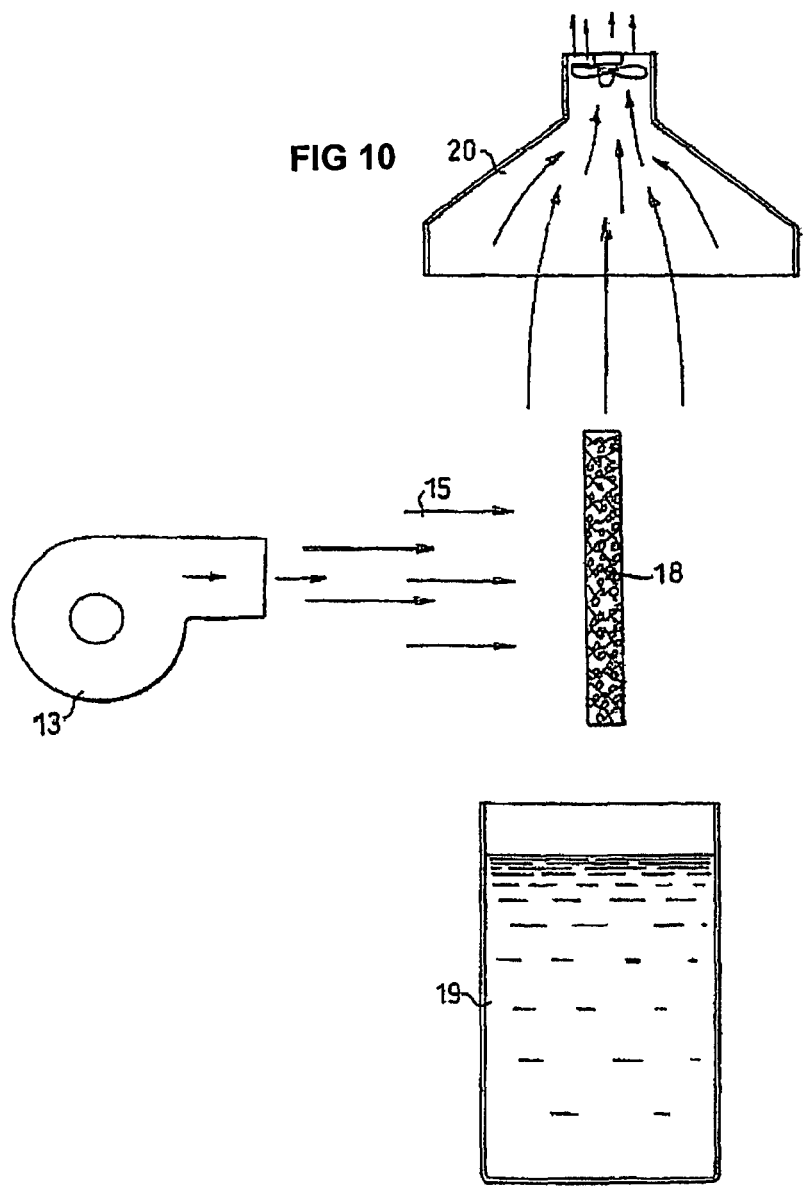

FIBERS OF VARIABLE WETTABILITY AND MATERIALS CONTAINING THE FIBERS

CROSS-REFERENCE TO RELATED APPLICATIONS

This application is a continuation of International Application Serial No. PCT/US04/043030, filed Dec. 20, 2004, which claims priority to U.S. Provisional Application Ser. No. 60/531,706, filed Dec. 19, 2003 and U.S. Provisional Application Ser. No. 60/569,980, filed May 10, 2004, each of which are incorporated by reference in their entireties herein, and from which priority is claimed.

FIELD OF THE INVENTION

The present invention is directed to an absorbent material, and the fibers therein, having variable wettability for the control of water absorption on the surface of the material.

BACKGROUND OF THE INVENTION

It has long been desirable to be able to control the surface characteristics of textiles and fabrics including nonwoven materials. A particularly important characteristic is whether a material readily absorbs or repels water at its surface. For fibers used to make nonwoven materials for use in personal care products and for many other uses, the relative hydrophobicity or hydrophilicity of the fiber itself, and the material made from it, is of great importance in determining where and how they can be used.

When brought into contact with the surface of a material, water prefers to wet some surfaces and prefers to bead on others. A surface can be classified as hydrophilic, with a water contact angle less than 90°, or hydrophobic, with a water contact angle greater than 90°, based on the shape that a drop of water assumes when placed on that surface.

Fabric water repellency and breathability have been studied for several decades (A. W. Adamson, Physical Chemistry of Surfaces, Second Edition, Wiley, 1967, Chapters VII and X). A nonwoven web of fibers can be modeled as a bundle of cylindrical pores (capillaries) of radius r. The fluid pressure required to penetrate the interfiber pores of a nonwoven web can be approximated from Laplace's equation for the penetration of a fluid into a tube as follows: $P=(2 \gamma \cos \theta)/r$ where:

P=pressure required to push fluid through the tube;
$\gamma$=fluid surface tension;
$\theta$=advancing contact angle; and
r=pore radius.

See Dutkiewicz, J., *Nonwoven Structures for Absorption of Body Fluids*, sub-chapter 2.1. Basic Structural Properties of Absorbent Networks, pages 7-37 (published by Edana, Brussels, Belgium) (2003). This equation can be used to describe web wetting ($\theta<90°$, P is positive) or web water repellency ($\theta>90°$, P is negative). In the case of water repellency, the fluid will not wet the web unless a pressure of P is applied to push the fluid into the web.

From the equation, barrier quality is predicted to be enhanced by increasing the contact angle with a water-repellent finish. In other words, the pores of the web should be rendered as hydrophobic as possible.

Apparent contact angles can be increased by surface roughness on the macroscale and microscale. Application of a waterproofing agent that causes microscopic pore surface roughness will lead to an increase in apparent contact angle, thus improving barrier quality.

From the equation, barrier quality is predicted to be enhanced by reducing the size of the interfiber pores. Ideally, the web should be as strong as possible. As pressure builds, weakness in the web will cause deformation, and deformation increases r, thus lowering pressure P. Web strength can be enhanced, for example, by increasing the amount of binder in the web.

The size of interfiber pores in a fibrous web is determined by the fiber size and the density or extent of compaction of the web. Increasing the density of the web can reduce the size of interfiber pores, or using smaller diameter fibers at the same density can reduce them. Smaller fibers pack together more efficiently in a densified web, resulting in smaller interfiber pores. From the equation, using smaller fibers serves to decrease r, thus raising pressure P.

Filler material can be added to an absorbent material to reduce the size of interfiber pores. From the equation, the addition of filler also serves to decrease r, thus raising pressure P.

From the equation, hydrophobicity and barrier quality is predicted to be directly proportional to the fluid surface tension. The barrier treatment should be as durable as possible. Any additives in the barrier treatment that will dissolve in the fluid coming in contact with the surface of the material will likely lower its surface tension, thus lowering pressure P.

SUMMARY OF THE INVENTION

The present invention provides for an absorbent material with two or more layers, including an upper layer which has on the outer surface one or more surface area zones. These zones include more wettable zones having greater hydrophilicity adjacent to less wettable zones. The treatment of the fibers in the absorbent material allow for the variable wettability of the present invention.

In certain aspects of the invention, the absorbent materials have more wettable zones with a total surface area which is from about 5 percent to about 95 percent of the upper surface layer. In a preferred embodiment, the more wettable zones have a total surface area which is from about 10 percent to about 90 percent of the upper surface layer, even more preferred, from about 30 percent to about 70 percent of the upper surface layer.

In another aspect of the invention, the more wettable zones of the absorbent material have elements in a pattern which are all connected, the elements of the pattern essentially isolating the less wettable zones from each other. Likewise, in another aspect of the invention, the less wettable zones have elements in a pattern which are all connected, the elements of the pattern essentially isolating the more wettable zones from each other.

In the absorbent material of the present invention, the less wettable zones of the upper surface layer contain a polyvalent metal ion salt of a fatty acid. In one embodiment of the invention, the more wettable zones of the absorbent material contain a polyvalent metal ion salt of a fatty acid and where the concentration of the polyvalent metal ion salt of a fatty acid is greater in the less wettable zones.

The present invention also provides for absorbent materials where the less wettable zones of the upper surface layer are located on protrusions which project above the surface of the material and the more wettable zones are located in indentations which project below the surface of the material. In another embodiment, the absorbent material has an upper less wettable layer and adjacent thereto a lower more wettable layer, where the upper less wettable layer has protrusions which project above the surface of the material and are at a greater distance from the lower layer than indentations which project below the surface of the upper layer and which are closer to the lower layer.

In yet another embodiment of the invention, the absorbent material is in the form of a sheet having an upper surface and opposite thereto a lower surface, where the entire upper surface is more wettable than the lower surface. In one aspect of this embodiment, the lower surface has disposed thereon a reaction product of a polyvalent cation-containing compound and a fatty acid containing compound.

In one aspect the present invention provides fibers bound with a polyvalent cation-containing compound and coated thereon with a fatty acid containing compound. In one embodiment, the fatty acid containing compound is present in an amount of from about 0.01 weight percent to about 5 weight percent based on the weight of the treated fiber, preferably from about 0.01 weight percent to about 3 weight percent based on the weight of the treated fiber, more preferably from about 0.05 weight percent to about 1.5 weight percent based on the weight of the treated fiber, and even more preferred, from about 0.1 weight percent to about 1 weight percent based on the weight of the treated fiber. In certain aspects of the invention, the fatty acid containing compound is selected from the group consisting of sodium oleate, methyl oleate, sodium laurate, oleic acid, stearic acid, and mixtures thereof.

In one embodiment, the polyvalent cation-containing compound is present in an amount from about 0.1 weight percent to about 20 weight percent based on the dry weight of the untreated fiber, preferably from about 2 weight percent to about 12 weight percent based on the dry weight of the untreated fiber, more preferably from about 3 weight percent to about 8 weight percent based on the dry weight of the untreated fiber. In one aspect of the invention, the polyvalent cation containing compound is a polyvalent metal ion salt, preferably selected from the group consisting of aluminum, iron, tin, salts thereof, and mixtures thereof. In a preferred embodiment, the polyvalent metal is aluminum. In other embodiments, the polyvalent salt is selected from the group consisting of aluminum chloride, aluminum hydroxide, aluminum sulfate, and mixtures thereof.

In one embodiment, the polyvalent cation-containing compound and fatty acid containing compound are directly applied to the fibers at a temperature close or above the melting point of the fatty acid. In one embodiment, the temperature ranges between about 110 to about 115 degrees Celsius.

The fatty acid may also be a component of a carrier in the form of particles. In one embodiment, the carrier is a type of fiber. In a preferred embodiment, the carrier is made of synthetic fibers. The carrier is blended with the cellulosic fibers and cured at a temperature to allow the carrier to melt or change into vapor.

In another embodiment of the invention, the fibers may further comprise a separate carrier. In certain embodiments, the carrier may be a type of fibers, preferably a polypropylene fiber. In one embodiment, the carrier comprises an acid. In a specific embodiment, the acid is stearic acid.

The fatty acid migrates and interacts or reacts with the cation on the surface of the fiber, forming as a reaction product a fatty acid salt. Migration can be accelerated or enhanced by heat. Thus, the fibers can be used to produce a fibrous material containing fibers which have disposed on the surface of the fiber a reaction product of a polyvalent cation-containing compound and a fatty acid containing compound. Fatty acid salts of polyvalent cations are generally characterized as having a very low water solubility or as being insoluble. In one form these materials are widely known as "bathtub ring". These materials are known waterproofing materials because of their hydrophobicity.

In the present invention, the contact angle of the fibers is equal to or greater than 90 degrees.

In another embodiment, the fibers further have a compound selected from the group consisting of an acid, a buffer salt, an insoluble metal hydroxide, and combinations thereof. Preferably, the compound is an acid more preferably a weak acid. In a preferred embodiment, the acid is citric acid. In one embodiment, the compound is present in an amount of from about 0.5 weight percent to about 10 weight percent based on the dry weight of the treated fibers, preferably from about 0.5 weight percent to about 3 weight percent based on the dry weight of the treated fibers.

In another aspect of the invention, the fibers also contain a reducing agent.

The fibers of the present invention may also be cross-linked optionally with treatment of a cross-linking agent. The fibers may be cross linked before, during, or after the fatty acid treatment. In one embodiment, the cross-linking agent is selected from the group consisting of formaldehyde, formaldehyde addition products, dialdehyde agents, and polycarboxylic acids. In another embodiment, the cross-linking agent is glutaraldehyde. In one aspect, the cross-lining agent is applied with thermal radiation.

In another aspect of this invention, the fibers are preswelled with a swelling agent prior to application of the fatty acid. In one embodiment, the swelling agent is a polyvalent metal salt, preferably sodium hydroxide.

The invention also provides for fibers treated with a polyvalent cation salt of a fatty acid directly applied to the fibers at a temperature close or above the melting point of the fatty acid. In one embodiment, the polyvalent cation salt is aluminum stearate. In another embodiment, the temperature ranges between about 110 to about 115 degrees Celsius.

In another aspect of this invention there is provided a blend of fibers comprising:
(A) fibers bound with a polyvalent cation-containing compound, and
(B) fibers coated with a fatty acid containing compound.

The invention also provides for fibrous material containing fibers which have disposed on the surface of the fiber a reaction product of a polyvalent cation-containing compound and a fatty acid containing compound. The fibrous material may also have one or more fillers.

The present invention also provides for a process of producing a hydrophobic fibrous material by:
(I) forming a fibrous material containing fibers bound with a polyvalent cation-containing compound and placing thereon a fatty acid containing compound, or
(II) forming a fibrous material containing a blend of fibers having
  (A) fibers bound with a polyvalent cation-containing compound, and
  (B) fibers coated with a fatty acid containing compound, and
(III) curing the material so that the polyvalent cation-containing compound and the fatty acid containing compound interact to form a product that renders the fibrous material hydrophobic.

In yet another aspect, the invention provides for a method for treating a solid material with a polyvalent metal containing compound and with a fatty acid containing compound, wherein the fatty acid containing compound is applied to the solid material in the form of a microdispersion; and a stream of gas is applied to the microdispersion of the fatty acid containing compound, so that the bonding of the fatty acid containing compound to the surface of the solid material is carried out by diffusion of the fatty acid containing compound in a heterogeneous medium onto all the surface of the solid material and reaction of the fatty acid containing compound with polyvalent metal containing compound bonded to the surface of the solid material. In one embodiment, the treatment of the surface of the solid material with a polyvalent metal containing compound is accomplished before the treatment of the surface of the solid material with a fatty acid containing compound in two separate steps. In another embodiment, the treatments are carried out in a continuous process. In order to produce a microdispersion of a fatty acid containing compound in one embodiment, a quantity of liquid composition of the fatty acid containing compound is applied in contact with the surface of the solid material.

In one method of the invention, the stream of gas is applied to the surface of the solid material. In another method, a stream of gas is applied to the solid material at the same time as a microdispersion of a fatty acid containing compound is produced. The gas is selected from the group consisting of ambient air, nitrogen, helium, carbon dioxide, and combinations thereof.

In one embodiment of the method, a microdispersion of the fatty acid containing compound is produced on the solid material before applying a stream of gas to the solid material. In another embodiment, a microdispersion of a fatty acid containing compound is produced by spraying directed towards the surface of the solid material. In yet another embodiment, the microdispersion of the fatty acid is applied in vapor form.

In another embodiment of the method, a microdispersion of a fatty acid containing compound is produced by contacting the surface of a first face of a solid support previously loaded with a liquid composition of the fatty acid containing compound. In another embodiment, a microdispersion of a fatty acid containing compound is produced by wetting the surface of the solid material with a liquid composition formed of a solution of the fatty acid containing compound in a volatile neutral solvent.

In one aspect of the invention, the solid support is selected from the group consisting of an absorbent pad, a non-absorbent pad, a roller driven in rotation, a brush, and mixtures thereof. The solid is wet by immersion in a bath of the liquid composition in one aspect.

In another aspect of the invention, the stream of gas is directed towards the surface of the solid material with a positive velocity component perpendicular to the surface of the solid material. The surface of the solid material is placed in a treatment space adapted according to the characteristics of the gas stream such that any quantity of gas flow coming from the solid material which can be once again returned to the solid material by the gas stream is negligible.

The invention also provides a method for forming a fibrous web containing first and second fibrous component, wherein a first component is treated with a fatty acid containing compound; a second component is treated with a polyvalent metal containing compound; and a stream of gas is applied to the fibrous web at a temperature allowing the fatty acid containing compound to transform to a vapor, so that the bonding of the fatty acid containing compound to the second component is carried out by diffusion of the fatty acid containing compound in a vapor state onto the second component and reaction of the fatty acid containing compound with polyvalent metal containing compound bonded to the second component. In one embodiment the polyvalent metal containing compound is replaced with a polyvalent organic cation.

Any of the methods of the invention may be used to treat a natural or artificial fiber or fibrous structure.

Various applications of the processes include obtaining a solid composition in a divided form, capable of absorbing hydrocarbons, and having a density of less than that of water. Another application is for treating paper. Yet another application of the processes of the invention are for treating the surface of glass.

DESCRIPTION OF THE DRAWINGS

FIG. 1A shows the foaming effect on a handsheet designated Web#2. FIG. 1B shows the foaming effect on handsheet Web#1. FIG. 1C shows an uncolored stain hide using the same Web#2, but without the blue pigment.

FIG. 3A illustrates an example of more wettable and less wettable zones with the use of a hydrophobic polymer containing a blue pigment. FIG. 3B illustrates uniform wettability in a handsheet without a textured surface.

FIG. 5A is an image of the top view and FIG. 5B is an image of the side view of the board. Both figures show the length of the upper board as 29.7 cm with the tube represented by (9).

FIG. 8 shows a sample of solid material placed under a rotating fan.

FIG. 9 shows a device, which can be used for continuous production of a hydrophobic sheet.

FIG. 10 shows another variant of a device, which can be used to produce a solid material with hydrophobic surface.

FIG. 11(*a*) shows the angle greater than 90 degrees demonstrating a hydrophobic surface. FIG. 11(*b*) shows the angle less than 90 degrees demonstrating a hydrophilic surface.

DETAILED DESCRIPTION

Figure 1A:
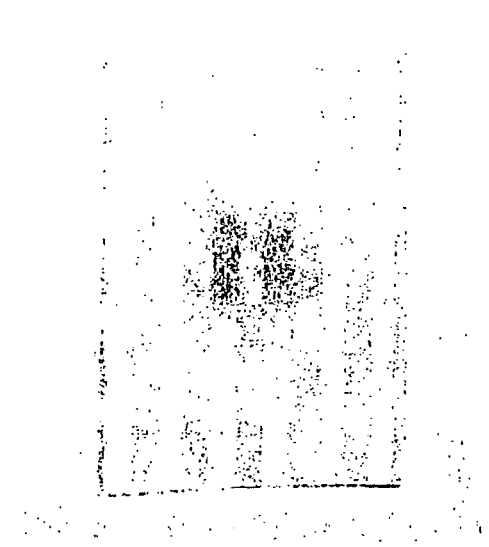
FIGS. 1A, 1B, and 1C represent the application of a foam coating on representative handsheets.
Figure 1B:
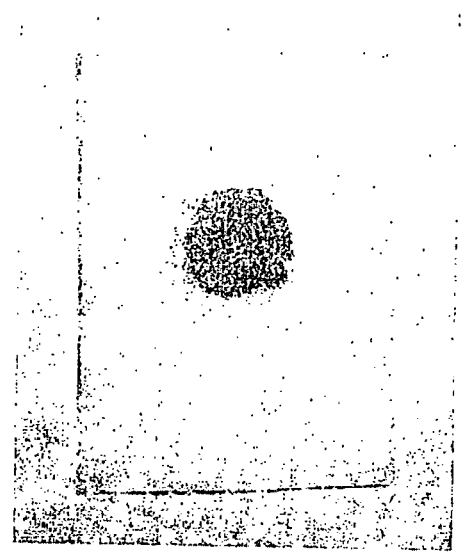

The absorbent materials of the present invention provide for multiple layers, including an upper layer with an outer surface of variable wettability zones. The fibers of the less wettable zones are treated with polyvalent-cation compounds and fatty acid compounds.

Cellulose Fibers

Cellulosic fibrous materials suitable for use in the present invention include softwood fibers and hardwood fibers. See M. J. Kocurek & C. F. B. Stevens, *Pulp and Paper Manufacture—Vol. 1: Properties of Fibrous Raw Materials and Their*

*Preparation for Pulping*, The Joint Textbook Committee of the Paper Industry, pp. 182 (1983), which is hereby incorporated by reference in its entirety. Exemplary, though not exclusive, types of softwood pulps are derived from slash pine, jack pine, radiata pine, loblolly pine, white spruce, lodgepole pine, redwood, and douglas fir. North American southern softwoods and northern softwoods may be used, as well as softwoods from other regions of the world. Hardwood fibers may be obtained from oaks, genus *Quercus*, maples, genus *Acer*, poplars, genus *Populus*, or other commonly pulped species. In general, softwood fibers are preferred due to their longer fiber length as measured by T 233 cm-95, and southern softwood fibers are most preferred due to a higher coarseness as measured by T 234 cm-84, which leads to greater intrinsic fiber strength as measured by breaking load relative to either northern softwood or hardwood fibers.

The fibrous material may be prepared from its natural state by any pulping process including chemical, mechanical, thermomechanical (TMP) and chemithermomechanical pulping (CTMP). These industrial processes are described in detail in R. G. Macdonald & J. N. Franklin, *Pulp and Paper Manufacture in 3 volumes; $2^{nd}$ Edition, Volume 1: The pulping of wood*, 1969; *Volume 2: Control, secondary fiber, structural board, coating*, 1969; *Volume 3: Papermaking and paperboard making*, 1970, The joint Textbook Committee of the Paper Industry, and in M. J. Kocurek & C. F. B. Stevens, *Pulp and Paper Manufacture, Vol. 1: Properties of Fibrous Raw Materials and Their Preparation for Pulping*, The Joint Textbook Committee of the Paper Industry, 1983, 182 pp., both of which are hereby incorporated by reference in their entirety. Preferably, the fibrous material is prepared by a chemical pulping process, such as a Kraft or sulfite process. In particular the Kraft process is especially preferred. Pulp prepared from a southern softwood by a kraft process is often called SSK. In a similar manner, southern hardwood, northern softwood and northern hardwood pulps are designated SHK, NSK and NHK, respectively. Bleached pulp, which is fibers that have been delignified to very low levels of lignin, are preferred, although unbleached kraft fibers may be preferred for some applications due to lower cost, especially if alkaline stability is not an issue. Desirably, the chemically treated cellulose fiber has been derived from a source which is one or more of Southern Softwood Kraft, Northern Softwood Kraft, hardwood, eucalyptus, mechanical, recycle and rayon, preferably Southern Softwood Kraft, Northern Softwood Kraft, or a mixture thereof, more preferably, Southern Softwood Kraft.

Pulp consistency is a pulp-industry specific term which is defined as the bone dry fiber amount divided by the total amount which includes fiber, water, other solids, etc. and multiplied by 100 percent. Therefore, for a slurry of 12 percent consistency, every 100 kilograms of slurry would contain 12 bone dry kilograms of fiber.

Chemically Treated Cellulose Fibers

As used herein, the phrase "chemically treated" cellulose fiber or non-cellulose fiber means a fiber that has been treated with a polyvalent metal-containing compound to produce a fiber with a polyvalent metal-containing compound bound to it.

It is not necessary that the compound chemically bond with the fibers, although it is preferred that the compound remain associated in close proximity with the fibers, by coating, adhering, precipitation, or any other mechanism such that it is not dislodged from the fibers during normal handling of the fibers. For convenience, the association between the fiber and the compound discussed above may be referred to as the bond, and the compound may be said to be bound to the fiber. It is necessary that the interaction of the materials used to produce the polyvalent metal-containing compound in proximity to the fibers or that the polyvalent metal-containing compound itself, dissociate into individual ions, preferably in an aqueous environment, and that the ions then contact individualized cellulose fibers. For example, sheeted cellulosic fibers treated with a water insoluble aluminum compound have the same aluminum concentration before and after hammer mill disintegration with a Kamas mill. Likewise, sheeted cellulosic fibers treated with a water soluble aluminum compound have the same aluminum concentration before disintegration with a Kamas mill and after disintegration with a Kamas mill. In addition, sheeted cellulosic fibers treated with a water insoluble and a water soluble aluminum compound have the same aluminum concentration before disintegration with a Kamas mill and after disintegration with a Kamas mill.

One type of chemically treated cellulose fiber which was originally developed for use in absorbent structures is described in U.S. Pat. No. 6,562,743 and a published counterpart, WO 00/38607, both of which are hereby incorporated by reference in their entirety. This fiber is available as CARESSA® from Buckeye Technologies Inc. of Memphis, Tenn. When used in absorbent structures, the chemically treated cellulose fiber has associated with it a weak acid. When used in other applications, for the fibers of this invention, it may be used with an associated weak acid, or in an alternative embodiment, it may be used without the associated weak acid.

The requirement that the polyvalent metal-containing compound be able to dissociate into individual ions or is formed from individual ions, preferably in an aqueous environment, and that the ions then contact individualized cellulose fibers, eliminates from further consideration as potentially useful as the polyvalent metal-containing compound of this invention many polyvalent metal-containing compounds and the fibers treated therewith, such as, for example, various clays used to treat fibers in paper making.

The chemically treated cellulose fiber or the chemically treated non-cellulosic fiber of this invention is treated with from about 0.1 weight percent to about 20 weight percent of the polyvalent metal-containing compound, based on the dry weight of the untreated fiber, desirably with from about 2 weight percent to about 12 weight percent of the polyvalent metal-containing compound, and preferably with from about 3 weight percent to about 8 weight percent of the polyvalent metal-containing compound.

Any polyvalent metal salt including transition metal salts may be used, provided that the compound is capable of increasing the stability of the cellulose fiber or the chemically treated non-cellulosic fiber in an alkaline environment. Examples of suitable polyvalent metals include beryllium, magnesium, calcium, strontium, barium, titanium, zirconium, vanadium, chromium, molybdenum, tungsten, manganese, iron, cobalt, nickel, copper, zinc, aluminum and tin. Preferred ions include aluminum, iron and tin. The preferred metal ions have oxidation states of +3 or +4. The most preferred ion is aluminum. Any salt containing the polyvalent metal ion may be employed. Examples of suitable inorganic salts of the above metals include chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, and hypophosphites. Examples of suitable organic salts of the above metals include formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, and 4,5-dihydroxy-benzene-1,3-disulfonates. In addition to the polyvalent metal salts, other compounds such as complexes of the above salts include amines, ethylenediaminetetra-acetic acid (EDTA), diethylenetriaminepenta-acetic acid (DIPA), nitrilotri-acetic acid (NTA), 2,4-pentanedione, and ammonia may be used. Preferred salts are aluminum chloride, aluminum hydroxide and aluminum sulfate.

Alum is an aluminum sulfate salt which is soluble in water. In an aqueous slurry of cellulose, some of the alum will penetrate the fiber cell wall, but since the concentration of ions is low, most of the dissolved aluminum salt will be outside the fiber. When the pH is adjusted to precipitate aluminum hydroxide, most of the precipitate adheres to the fiber surface.

In one embodiment of this invention, the chemically treated cellulose fiber or the chemically treated non-cellulosic fiber has an acid bound or otherwise associated with it. A variety of suitable acids may be employed, although the acid preferably should have a low volatility, and bond to the fiber. Strong mineral acids are not suitable, and, preferably, the acid used in the practice of this aspect of this invention is a weak acid. Examples include inorganic acids such as sodium bisulfate, sodium dihydrogen phosphate and disodium hydrogen phosphate, and organic acids such as formic, acetic, aspartic, propionic, butyric, hexanoic, benzoic, gluconic, oxalic, malonic, succinic, glutaric, tartaric, maleic, malic, phthallic, sulfonic, phosphonic, salicylic, glycolic, citric, butanetetracarboxylic acid (BTCA), octanoic, polyacrylic, polysulfonic, polymaleic, and lignosulfonic acids, as well as hydrolyzed-polyacrylamide and CMC (carboxymethylcellulose). Among the carboxylic acids, acids with two carboxyl groups are preferred, and acids with three carboxyl groups are more preferred. Of these acids, citric acid is most preferred.

In general, the amount of acid employed is dictated by the acidity and the molecular weight of that acid. Generally, it is found that an acceptable range of acid application is from about 0.5 weight percent of the fibers to about 10 weight percent of the fibers. As used herein, the "weight percent of the fibers" refers to the weight percent of dry fiber treated with the polyvalent metal containing compound. For citric acid, the preferred range of application is from about 0.5 weight percent to about 3 weight percent of the fibers. A preferred combination is an aluminum-containing compound and citric acid. For the chemically treated fibers of this aspect of this invention, it is desirable that the weak acid content of the chemically treated fibers is from about 0.5 weight percent to about 10 weight percent based on the dry weight of the treated fibers, more desirably, from about 0.5 weight percent to about 5 weight percent based on the dry weight of the treated fibers, and, preferably, from about 0.5 weight percent to about 3 weight percent based on the dry weight of the treated fibers.

Within the scope of this aspect of this invention is the use of buffer salts rather than a weak acid in combination with the polyvalent metal-containing compound. Any buffer salt that in water would provide a solution having a pH of less than about 7 is suitable. Examples of these are sodium acetate, sodium oxalate, sodium tartrate, sodium phthalate, sodium dihydrogen phosphate, disodium hydrogen phosphate and sodium borate. Buffer salts may be used in combination with their acids in a combination that in water would provide a solution having a pH of less than about 7, for example, oxalic acid/sodium oxalate, tartaric acid/sodium tartrate, sodium phthalate/phthalic acid, and sodium dihydrogen phosphate/disodium hydrogen phosphate.

In a further variation of this invention, the polyvalent metal-containing compound is used in combination with an insoluble metal hydroxide, such as, for example, magnesium hydroxide, or in combination with one or more alkali stable anti-oxidant chemicals or alkali stable reducing agents that would inhibit fiber degradation in an alkaline oxygen environment. Examples include inorganic chemicals such as sodium sulfite, and organic chemicals such as hydroquinone.

For the chemically treated fibers of this aspect of this invention, in combination with the polyvalent metal-containing compound, it is desirable that the buffer salt content, the buffer salt weak acid combination content, the insoluble metal hydroxide content and/or the antioxidant content of the chemically treated fibers is from about 0.5 weight percent to about 10 weight percent based on the dry weight of the treated fibers, more desirably, from about 0.5 weight percent to about 5 weight percent based on the dry weight of the treated fibers, and, preferably, from about 0.5 weight percent to about 3 weight percent based on the dry weight of the treated fibers.

If desired, reducing agents may be applied to the treated fibers to maintain desired levels of fiber brightness, by reducing brightness reversion. The addition of acidic substances may cause browning of fibers when heated during processing of webs containing the fibers. Reducing agents counter the browning of the fibers. The reducing agent should also bond to the fibers. Preferred agents are sodium hypophosphite and sodium bisulfite and mixtures thereof.

The fibers suitable for use in the practice of this invention may be treated in a variety of ways to provide the polyvalent metal ion-containing compound in close association with the fibers. A preferred method is to introduce the compound in solution with the fibers in slurry form and cause the compound to precipitate onto the surface of the fibers. Alternatively, the fibers may be sprayed with the compound in aqueous or non-aqueous solution or suspension. The fibers may be treated while in an individualized state, or in the form of a web. For example, the compound may be applied directly onto the fibers in powder or other physical form. Whatever method is used, however, it is preferred that the compound remain bound to the fibers, such that the compound is not dislodged during normal physical handling of the fiber before contact of the fiber with liquid.

In a preferred embodiment, the treated fibers of the present invention are made from cellulose fiber known as FOLEY FLUFFS® from Buckeye Technologies Inc. (Memphis, Tenn.). The pulp is slurried, the pH is adjusted to about 4.0, and aluminum sulfate $(Al_2(SO_4)_3)$ in aqueous solution is added to the slurry. The slurry is stirred and the consistency reduced. Under agitation, the pH of the slurry is increased to approximately 5.7. The fibers are then formed into a web or sheet, dried, and, optionally, sprayed with a solution of citric acid at a loading of about 2.5 weight percent of the fibers. The web is then packaged and shipped to end users for further processing, including fiberization to form individualized fibers useful in the manufacture of various products.

In another preferred embodiment, the treated fibers of the present invention are made from cellulose fiber obtained from Buckeye Technologies Inc. (Memphis, Tenn.). The pulp is slurried, the pH is adjusted to about 4.0, and aluminum sulfate $(Al_2(SO_4)_3)$ in aqueous solution is added to the slurry. The slurry is stirred and the consistency reduced. Under agitation, the pH of the slurry is increased to approximately 5.7. The fibers are then formed into a web or sheet, dried, and sprayed with a solution of sodium oleate at a loading of about 1.0 weight percent of the fibers. The web is then packaged and shipped to end users for further processing, including re-slurrying to form a web useful in the manufacture of filtration products. If a reducing agent is to be applied, preferably it is applied before a drying step and following any other application steps. The reducing agent may be applied by spraying, painting or foaming.

Metal ion content, including aluminum or iron content, in pulp samples is determined by wet ashing (oxidizing) the sample with nitric and perchloric acids in a digestion apparatus. A blank is oxidized and carried through the same steps as the sample. The sample is then analyzed using an inductively coupled plasma spectrophotometer, such as, for example, a Perkin-Elmer ICP 6500. From the analysis, the ion content in the sample can be determined in parts per million. The polyvalent cation content desirably is from about 0.1 weight percent to about 5.0 weight percent, based on the dry weight of the treated fibers, more desirably, from about 0.1 weight percent to about 3.0 weight percent, based on the dry weight of the treated fibers, preferably from about 0.1 weight percent to about 1.5 weight percent, based on the dry weight of the treated fibers, more preferably, from about 0.2 weight percent to about 0.9 weight percent, based on the dry weight of the treated fibers, and more preferably from about 0.3 weight percent to about 0.8 weight percent, based on the dry weight of the treated fibers.

Without intending to be bound by theory, it is believed that by this process, the soluble $Al_2(SO_4)_3$ introduced to the pulp slurry is converted to insoluble $Al(OH)_3$ as the pH is increased. The insoluble aluminum hydroxide precipitates onto the fiber. Thus, the resultant chemically treated cellulose fibers are coated with $Al(OH)_3$ or contain the insoluble metal within the fiber interior.

The sodium oleate sprayed onto the web containing the fibers dries on the fibers. When the $Al(OH)_3$-oleate treated fibers are formed into a filter based sheet, the aluminum and oleate ions create a hydrophobic environment in addition to increasing the wet strength of the structure. These results are exemplified in the procedures set forth below.

In another embodiment, hydrated aluminum sulfate and sodium oleate are sprayed on the fiber after the drying section of a paper machine. In another embodiment, hydrated aluminum sulfate and sodium oleate are precipitated onto the fiber in the wet end section of a paper machine. In another embodiment, hydrated aluminum sulfate and sodium hypophosphite are sprayed on the fiber prior to the pressing stage, and sodium oleate is sprayed after drying. In another embodiment, hydrated aluminum sulfate, sodium hypophosphite and sodium oleate are sprayed on the fiber prior to the pressing stage. In yet another embodiment, hydrated aluminum sulfate is precipitated onto the fiber, hydrated aluminum and sodium hypophosphite are sprayed on the fiber prior to pressing, and sodium oleate is sprayed on the fiber after drying. In another embodiment, hydrated aluminum sulfate is precipitated onto the fiber and sodium oleate is sprayed on the fiber prior to the pressing stage.

Various materials, structures and manufacturing processes useful in the practice of this invention are disclosed in U.S. Pat. Nos. 6,241,713; 6,353,148; 6,353,148; 6,171,441; 6,159,335; 5,695,486; 6,344,109; 5,068,079; 5,269,049; 5,693,162; 5,922,163; 6,007,653; 6,355,079; 6,403,857; 6,479,415; 6,562,742; 6,562,743; 6,559,081; 6,495,734; 6,420,626; and in U.S. Patent applications with serial numbers and filing dates, 09/719,338 filed Jan. 17, 2001; Ser. No. 09/774,248 filed Jan. 30, 2001; and Ser. No. 09/854,179 filed May 11, 2001, all of which are hereby incorporated by reference in their entirety.

All patents, patent applications, and publications cited in this specification are hereby incorporated by reference in their entirety. In case of a conflict in terminology, the present disclosure controls.

Fatty Acid Containing Compounds

A very large number of natural and synthetic fatty acids and various derivatives are known. Examples of some useful in the practice of the present invention are listed below:

Monocarboxylic, straight, saturated acids such as butyric, valeric, caproic, caprylic, pelargonic, capric, lauric, myristic, palmitic, margaric, stearic, arachidic, behenic, lignoceric, cerotic, carboceric, montanic, mellisic, lacceroic, ceromelissic, and geddic; monocarboxylic, straight, unsaturated acids such as palmitoleic, oleic, linoleic, alpha-linoleic, arachdonic, 5,8,11,14,17-eicosapentaenoic (EPA), 4,7,10,13,16,19-docosahexaenoic (DHA); branched-chain fatty acids such as tuberculostearic, phytomonic, mycolipenic, mycocerosic, phytanic, pristanic; and dicarboxylic acids such as oxalic, malonic, adipic, succinic, glutaric, pimelic, suberic, azelaic, sebacic, alkilitaconates such as chaetomellic and ceriporic. Other fatty acids and various derivatives include mono-, di- and triglycerides, polyglycerol esters, alkyl alcohol esters, aromatic alcohol esters, phenol esters, amides, amino acids, hydroxyacids, fatty acid salts, phospholipids, bile acids such as cholic, and chenodeoxycholic.

Various commercially available materials include fatty acids and derivatives derived from animal and vegetable sources. Some examples are listed as follows: Animal fatty acid (distilled Tallow F.A.); Caprylic/capric acid blend; Caproic acid; Caprylic acid; Distilled coconut fatty acid; Coconut Fatty Acid; Distilled mixed fatty acid; Distilled palm fatty acid; Distilled rice bran fatty acid; Distilled soya bean fatty acid; Lauric acid; Myristic acid; Norfox oleic acid; Oleic acid; Olive oleic acid 75; Palmitic acid; Soap fatty acid; Specially formulated distilled coco F.A.; Specially formulated distilled tallow F.A.; Stearic acid; Vegetable stearic acid; Tall oil fatty acid substitute; Tall Oil Fatty Acids; Tallow fatty acid; Uniquema fatty acids; Butyl oleate; Butyl stearate; Calcium stearate; Cetostearyl alcohol; Cetyl alcohol; Cetyl palmitate; Decyl oleate; Diacetin; Ethyl linoleate; Ethyl oleate; Ethyleneglycol distearate; Ethyleneglycol monostearate; Ethylhexanoic acid; 2-Ethylhexyl cocoate; 2-Ethylhexyl oleate; 2-Ethylhexyl palmitate; 2-Ethylhexyl stearate; 2-Ethylhexyl tallowate; Glyceryl monococoate; Glyceryl monolaurate; Glyceryl monooleate; Glyceryl monostearate; Glyceryl tricaprylate/caprate, Glyceryl trioleate; 12-Hydroxystearic acid; Isobutyl oleate; Isobutyl stearate; Isopropyl myristate; Isopropyl oleate; Isopropyl palmitate; Isostearyl isostearate; Isotridecyl stearate; Lauric acid; Linseed fatty acids; Linseed oil methyl ester; Magnesium stearate; Methyl cocoate; Methyl laurate; Methyl oleate; Methyl ricinoleate; Methyl stearate; Methyl tallate; Methyl tallowate; Myristic acid; Neopentylglycol dioleate; Octyl cocoate; Octyl oleate; Octyl palmitate; Octyl stearate; Octyl tallowate; Octyldodecanol; Oleic acid; Oleyl alcohol; Oleyl erucate; Oleyl oleate; Palmitic acid; Pelargonic acid; Pentaerythritol tetraoleate; Propyleneglycol; caprylate/caprate; Propyleneglycol dioleate; Propyleneglycol dipelargonate; Propyleneglycol monostearate; Propyleneglycol ricinoleate; Rapeseed methyl ester; Ricinoleic acid; Sorbitan monolaurate; Sorbitan monooleate; Sorbitan monopalmitate; Sorbitan monostearate; Sorbitan trioleate; and Sorbitan tristearate.

Below in Table 1 is a listing of fatty acid containing compounds useful in the practice of this invention.

TABLE 1

| Common name acid | Structure | Source |
|---|---|---|
| Acetic | 2:0 | Platelet activating factor |
| Acrylic | 2e-3:1 | Nnc |
| Adipic | 6:0 di-acid | Nnc |
| Adrenic | 7c10c13c16c-22:4 | Adrenal lipids |
| Agonandoic (aka. ximenynic) | 9a,11t-18:2 | *Santalum acuminatum* |
| Agonandric | 8-OH 9a11t-18:2 | *Agonandra* (*Opiliaceae*) |
| Alchornoic | cis-14, 15-ep 11c-20:1 | *Alchornia cordifolia* |
| Alepramic | 3-Cp 3:0 | *Flacourtiaceae* seed oils |
| Aleprestic | 5-Cp 5:0 | *Flacourtiaceae* seed oils |
| Alepric | 9-Cp 9:0 | *Flacourtiaceae* seed oils |
| Aleprolic | 1-Cp 1:0 | *Flacourtiaceae* seed oils |
| Aleprylic | 7-Cp 7:0 | *Flacourtiaceae* seed oils |
| Aleuritic | 9,10,16-triOH 16:0 | Shellac |
| Ambrettolic | 16-OH 7c-16:1 | Musk mellon seed oil |
| Angelic | 2Me 2c-4:1 | *Angelica archangelica* |
| Anteisoheptadecanoic | 14Me 16:0 | Animal fats |
| Anteisononadecanoic | 16Me 18:0 | Animal fats |
| Anteisopentadecanoic | 12Me 14:0 | Animal fats |
| Anteisotridecanoic | 10Me 12:0 | Animal fats |
| Arachidic | 20:0 | Groundnut (peanut) oil |
| Arachidonic | 5c8c11c14c-20:4 | Animal phospholipids |
| Argenonic | 6-OH, 6-Me, 9-oxo-28:0 | *Papaveraceae* |
| Artemesic | See Coriolic | — |
| Asclepic | 11c-18:1 | *Asclepia* oils |
| Ascorbic | Vitamin C | — |
| Auricolic | 14-OH 11c17c-20:2 | *Lesquerella auriculata* |
| Avenoleic | 15(R)-OH 9c12c-18:2 | |
| Axillarenic | 11,13-di OH, 9c-24:1 | *Euphorbiaeceae* |
| Azelaic | 9:0 di-acid | Nnc |
| Behenic | 22:0 | *Lophira alata* |
| Behenolic | 13a-22:0 | Nnc |
| Bishomopinolenic | 7c,11c,14c-20:3 | |
| Bolekic | 9a11a13c-18:3 | Isano oil |
| Bosseopentaenoic | 5c8c10t12t14c-20:5 | *Bossiella orbigniana* |
| Brassidic | 13t-22:1 | Trans form of erucic acid |
| Brassylic | 13:0 di-acid | Nnc |
| Buiolic (jalapinolic) | 11-OH 16:0 | |
| Butolic | 6-OH 14:0 | Shellac |
| Butyric | 4:0 | Milk fats |
| Calendic (α) | 8t10t12c-18:3 | *Calendula officinalis* |
| Calendic (β) | 8t10t12t-18:3 | Trans form of α-calendic acid |
| Capric | 10:0 | Lauric oils |
| Caproic | 6:0 | Milk fats |
| Caproleic | 9c-10:1 | Milk fats |
| Caprylic | 8:0 | Lauric oils |
| Carboceric | 27:0 | — |
| Catalpic | 9t11t13c-18:3 | *Catalpa ovata* |
| Cerebronic | 2-OH 24:0 | Cerebrosides |
| Cerinic | See Cerotic | — |
| Ceromelissic | 33:0 (see psyllic) | — |
| Ceroplastic | 35:0 | Nnc |
| Cerotic | 26:0 | Waxes |
| Cervonic | DHA | — |
| Cetelaidic | 11t-20:1 | Hydrogenated fish oils |
| Cetoleic | 11c-22:1 | Fish oils |
| Chaulmoogric | 13-Cp 13:0 | Flacourtiaceae seed oils |
| Chrysobalanic | 4-oxo 9c11t13t15c-18:4 | *Chyrsobalanus icaco* |
| Civetic | 8t-17:1 di-acid | |
| CLA | Conjugated 18:2 isomers | Ruminant fats |
| Clupadonic | 7c10c13c16c19c-22:5 | Fish oils |
| Colneleic | 9-oxa-8t10t12c-18:3 | Enzymic oxidation of linoleic acid |
| Colnelenic | 9-oxa-8t10t12c15c-18:4 | Enzymic oxidation of linolenic acid |
| Columbinic | 5t9c12c-18:3 | *Aquilegia vulgaris* |
| Coniferonic | 5c,9c,12c,15c-18:4 | Conifer |
| Convolvulinolic | 11-OH 14:0 | Ipomea oils |
| Coriolic | 13-OH 9c11t-18:2 | *Xeranthemum annuum* |
| Coronaric | Cis-9,10-ep 12c-18:1 | *Chrysanthemum coronarium* |
| Couepic | See Licanic | — |
| Couepinic (licanic?) | 4-keto 9c11c13c-18:3; | — |
| Crepenynic | 9c12a-18:2 | *Crepis* and *Afzelia* oils |
| Daturic | See Margaric | Animal fats |
| Dehydrocrepenyic | 9c12a14c-18:3 | — |
| Demospongic | C24–C34 5c9c-diene acids | Sponges |
| Densipolic | 12(R)-OH 9c15c-18:2 | *Lesquerella densipila* |

TABLE 1-continued

| Common name acid | Structure | Source |
|---|---|---|
| DHA | 4c7c10c13c16c19c-22:6 | Fish oils |
| *Dicramin | 9c12c15c6a-18:4 | *dicramium scoparium* |
| Dihomolinoleic | 11c14c-20:2 | |
| Dihomolinolenic | 8c11c14c-20:3 | Animal fats |
| Dihomo Mead's acid | 7c10c13c-22:3 | |
| Dihomopinolenic | 7c11c14c-20:3 | Pinacae family |
| Dihomotaxoleic | 7c11c-20:2 | *Taxus* spp. |
| Dihydroxystearic | 9,10-diOH 18:0 | — |
| *Dimorphecolic | 9-OH, 10t, 12t-18:2 | *Dimorphecolic pluvialis* |
| DPA | 7c10c13c16c19c-22:5 | Fish oils |
| Elaidic | 9t-18:1 | Trans isomer of oleic acid |
| Elaidolinolenic | See Linolenelaidic | — |
| EPA | 5c8c11c14c17c-20:5 | Fish oils |
| Eleostearic (α) | 9c11t13t-18:3 | Tung oil |
| Eleostearic (α) | 9c11t13t-18:3 | *Momordica charantia*** |
| Eleostearic (β) | 9t11t13t-18:3 | All-trans α-eleostearic acid |
| Enanthic | 7:0 | Nnc |
| Ephedrenic | 5c,11c-18:2 | Ephedra |
| Erucic | 13c-22:1 | *Cruciferae* seed oils |
| Erythrogenic | See Isanic | — |
| Exocarpic | 9a11a13t-18:3 | Isano oil |
| Gadelaidic | 9t-20:1 | Trans form of gadoleic acid |
| Gadoleic | 9c-20:1 | Fish oils |
| Gaidic | 2t-16:1 | — |
| Geddic | 34:0 | — |
| Gheddic | 34:0 | — |
| GLA | 6c9c12c-18:3 | Evening primrose, borage, etc |
| Glutaric | 5:0 di-acid | Nnc |
| Gondoic | 11c-20:1 | Fish oils |
| *Gondoleic | 9c-20:1 | — |
| Gorlic | 13-Cp 6c-13:1 | *Flacourticeae* oils |
| Helenynolic | 9-OH 10t12a-18:2 | *Helychrysum bracteatum* |
| *Hiragonic | 7c10c13c-16:3 | Fish oils |
| Hormelic | 15-Cp 15:0 | *Flacourticeae* oils |
| Hydnocarpic | 11-Cp 11:0 | *Flacourticeae* oils |
| *Hydrosorbic | 3e-16:1 di-acid | — |
| Hydroxycerebronic | 2-hydroxycerebronic | *Sphingolipids* |
| Hydroxynervonic | 2-hydroxynervonic | *Sphingolipids* |
| Ipurolic | 3,11-diOH 14:0 | *Ipomoca* oils |
| Isanic | 9a11a17e-18:3 | Isano oil |
| Isanolic | 8-OH 9a11a17e-18:3 | Isano oil |
| Isoarachidic | 18-Me 19:0 | — |
| Isobutyric | 2-Me 3:0 | — |
| Isocaproic | 4-Me 5:0 | — |
| Isocerotic | 24-Me 25:0 | — |
| Isoheptadecanoic | 15-Me-16:0 | — |
| Isolauric | 10-Me-11:0 | — |
| Isomargaric | 15-Me 16:0 | — |
| Isomontanic | 26-Me-27:0 | — |
| *Isomycomycin | 3c5c7a9a11a-13:5 | — |
| Isomyristic | 12-Me 13:0 | — |
| Isononadecanoic | 17-Me 18:0 | — |
| Isopalmitic | 14-Me 15:0 | — |
| Isopentadecanoic | 13-Me 14:0 | — |
| Isoricinoleic | 9-OH, 12c-18:1 | *Strophanthus* |
| Isostearic | 16-Me-17:0 | — |
| Isotridecanoic | 11-Me 12:0 | — |
| *Isovaleric | 3-Me 4:0 | Porpoise, dolphin |
| Jacaric | 8c10t12c-18:3 | *Jacaranda mimosifolia* |
| Jalapinolic | 11-OH 16:0 | Jalap resin |
| Japanic | 21:0 di-acid | — |
| Jasmonic | C12 cyclopentane acid | Linoleic acid metabolite |
| Juniperic | 16-OH 16:0 | Conifer waxes |
| Juniperinic | 16-OH 16:0 | Conifer waxes |
| Juniperonic | 5c11c14c17c-20:4 | Conifer waxes |
| Kamlolenic (α) | 18-OH 9c11t13t-18:3 | Kamala oil |
| *Kamlolenic (β) | 18-OH 9t11t13t-18:3 | Kamala oil |
| *Kerrolic | 4-OH-16:0 | Shellac |
| Keteleeronic | 5c11c-20:2 | *Gymnosperm* sp |
| Labellenic | 5,6-18:2 (R)-form | *Leonotis* seed oil |
| Lacceric | 32:0 | Stick lac wax |
| Lacceroic | See lacceric | Stick lac wax |
| Lactarinic | 6-oxo 18:0 | *Lactarius rufus* |
| Lanoceric | di-OH 30:0 | — |
| Lamenallenic | 5,6,16t-18:3 | *Laminium purpureum* |
| Lactobacillic | 11,12-Mt 18:0 | Micro-organisms |
| Lauric | 12:0 | Lauric oils |
| Lauroleic | 9c-12:1 | — |

TABLE 1-continued

| Common name acid | Structure | Source |
|---|---|---|
| Lesquerolic | 14-OH 11c-20:1 | *Lesquerella* spp |
| Levulinic (aka levulic) | 4-oxo-5:0 | |
| Licanic (α) | 4-oxo 9c11t13t-18:3 | *Licania rigida* |
| Licanic (β) | 4-oxo 9t11t13t-18:3 | Trans-form of α-licanic acid |
| Lignoceric | 24:0 | Waxes |
| Linelaidic | 9t12t-18:2 | All-trans form of linoleic acid |
| Linderic | 4c-12:1 | *Lindera obtusiloba* |
| Linoleic__ | 9c12c-18:2 | All seed oils |
| Linolenelaidic | 9t12t15t-18:3 | All-trans form of linolenic acid__ |
| Linolenic__ | 9c12c15c-18:3 | Linseed |
| Lumequic | 21c-30:1 | *Ximenia* spp |
| Linusic | 9,10,12,13,15,16-OH 18:0 | From linolenic acid |
| Malonic | 3:0 di-acid__ | — |
| Malvalic | 8,9-Mt 8c-17:1 | Cottonseed oil |
| Manaoic | 11-Cp 6c-11:0 | *Flacourtiaceae* seed oils |
| Mangold's acid | 9t11t-18:2 | — |
| Margaric | 17:0 | Animal fats |
| Margarolic | 9c-17:1 | |
| Mead's acid | 5c8c11c-20:3 | Metabolite of oleic acid__ |
| Megatomic | 3t5c-14:2 | Black carpet beetle pheromone |
| Melissic | 30:0 | Bayberry |
| Mikusch's acid | 10t12t-18:2 | — |
| Montanic | 28:0 | Waxes (ie. carnuba) |
| Moroctic | See stearidonic | — |
| Morotic | See stearidonic | — |
| Mycoceranic | 2,4,6-triMe 26:0 | *Tubercle bacilli* |
| Mycocerosic | See mycoceranic | — |
| Mycolic | RCHOHCH(R')COOH | Mycobacteria |
| Mycolipenic | 2,4,6-tri-Me-2t-24:1 | *tuburele bacilli* |
| Mycomycin | 3t5c7,8,10a12a-13:6 | — |
| Myristelaidic | 9t-14:1 | Trans form of myristoleic acid |
| Myristic | 14:0 | Lauric oils |
| Myristoleic | 9c-14:1 | |
| Nemotinic | 4e6a8a10a-11:4 | — |
| *Nemotinic__ | 4-OH, 5,6,8a,10a-11:4 | *Basidomycetis* moulds |
| Nervonic | 15c-24:1 | Honesty seed oil, nerve tissue |
| Nisinic | 6c9c12c15c18c21c-24:6 | Fish oils |
| Obtusilic | 4c-14:1 | *Lindera obtusiloba* |
| Oleic | 9c-18:1 | All oils and fats |
| Oncobic | 15-Cp 8c-15:0 | *Flacourtiaceae* seed oils |
| Osband's acid | See DPA | — |
| Oxalic | 2:0 di-acid | — |
| Paullinic | cis-13-eicosenoic acid | |
| Palmitelaidic | 9t-16:1 | Trans form of palmitoleic acid__ |
| Palmitic | 16:0 | All oils and fats |
| Palmitoleic | 9c-16:1 | Fish oils, macadamia oil |
| Parinaric (α) | 9c11t13t15c-18:4 | *Parinarium laurinum* |
| Parinaric (β) | 9t11t13t15t-18:4 | Trans-form of α-parlnaric acid |
| Pelargonic | 9:0 | — |
| Petroselaidic | 6t-18:1 | Trans form of petroselinic acid__ |
| Petroselinic | 6c-18:1 | *Umbelliferae* oils |
| Phellonic | 22-OH 22:0 | Cork |
| Phloionolic | 9S10S18S-triOH 18:0 | Cork |
| Phlomic | 7,8-20:2 | |
| *Phthioic | 3,13,19-triMe 23:0 | — |
| Phrenosic | See cerebronic | — |
| Phrenosinic | See cerebronic | — |
| Phthianoic | See mycoceranic | — |
| Phthioic | Polybranched acids | Micro-organisms |
| Physeteric | 5c-14:1 | Whale oil |
| Physetoleic | See Palmitoleic | — |
| Phytanic__ | 3,7,11,15-tetraMe 16:0 | Marine animal fats |
| *Phytenic | See Phytenoic | — |
| Phytenoic | 3,7,11,15-tetraMe 2e-16:1 | Marine animal fats |
| Phytomonic | See Lactobacillic | — |
| Pimelic__ | 7:0 di-acid | — |
| Pinolenic | 5c9c12c-18:3 | *Toucrium depressum* |
| Podocarpic | 5c11c14c-20:3 | *Podocarpus nagera* |
| Pristanic | 2,6,10,14-tetraMe 15:0 | Marine animal fats |
| Pseudoeleostearic | 10t12t14t-18:3 | Isomerized linolenic acid__ |
| Psyllic | 33:0 | — |
| Punicic | 9c11t13c-18:3 | *Punica granatum* |
| Punicic | 9c11t13c-18:3 | *Trichosanthes anguina** |
| Pyrulic | 8a10t-17:2 | *Pyrularia pubera* |
| Ricinelaidic | 12-OH 9t-18:1 | Trans form of ricinoleic acid__ |
| Ricinoleic | 12-OH 9c-18:1 | Castor oil |

TABLE 1-continued

| Common name acid | Structure | Source |
|---|---|---|
| Rosilic | 10-OH 18:0 | Leaf waxes |
| Rumenic | 9c11t-18:2 | Ruminant fats |
| Sabinic | 12-OH 12:0 | *Juniperus oxycedrus* leaves |
| Santalbic | See ximenynic | — |
| Sativic | 9,10,12,13-tetraOH 18:0 | From oxidation of linoleic acid_ |
| Sciadonic | 5c11c14c-20:3 | *Pinus* species |
| *Scoliodonic | 24:5_ | — |
| Sebacic | 10:0 di-acid | — |
| Selacholeic | 15c-24:1 (see nervonic) | Shark liver oils |
| Shibic | 26:5 | Fish oils |
| *Sorbic | 2t4t-6:2 di-acid | — |
| Stearic | 18:0 | Animal fats, cocoa butter |
| Stearidonic | 6c9c12c15c-18:4 | *Echium* oils, fish oils |
| Stearolic | 9a-18:1 | *Santalaceae* |
| Sterculic | 9,10-Mt 9c-18:1 | Cottonseed oil |
| Sterculynic | 9,10-Mt 9c17a-18:2 | *Sterculia alata* |
| Stillingic | 2c4t-10:2 | *Sepium sebiferum* |
| Strophanthus | 9-OH,12c-18:1 | *Apocyanaceae* |
| Suberic | 8:0 di-acid_ | — |
| Succinic | 4:0 di-acid | — |
| Tariric | 6a-18:1 | *Picramnia* spp |
| Taxoleic | 5c9c-18:2 | *Gymnospermae* seed lipids |
| Thapsic (or thaspic) | 16:0 di-acid | Waxes |
| Thynnic | 26:6 (probably n-3) | Fish oils |
| Timnodonic (see EPA) | 4c8c12c15c18c-20:5c** | — |
| Traumatic | 2t-20:1 di-acid | — |
| Trichosanic | See punicic | — |
| Tsuduic | 4-14:1 | *Lindera obtisiloba* |
| Tsuzuic | 4-14:1 | *Lindera obtisiloba* |
| Tuberculostearic | 10-Me 18:0 | *Tubercle bacilli* |
| Undecylenic | 10e-11:1 | Castor oil |
| Ustilic | 15,16-diOH 16:0 | Ustilagic acid (antibiotic) |
| Vaccenic | 11t-18:1 | Ruminant fats |
| Valeric | 5:0 | — |
| Vernolic | 12,13-ep, 9c-18:1 | *Vernonia* oils |
| Wyerone acid | 2c,(3,4-F*),5a7c-10:3 | *Exocarpus cupressiformis* |
| Ximenic | 17c-26:1 | *Ximenia americana* |
| Ximenynic | 9a11t-18:2 | *Santalum acuminatum* |
| Ximenynolic | 8-OH, 9a11t-18:2 | — |
| Zoomaric | See palmitoleic | — | c = cis,
t = trans,
a = acetylene
e = ethylenic bond (stereochemistry not relevant or unknown)
ep = epoxy
Me = methyl group
Mt = methano —$CH_2$— Cp = 2-cyclopentenyl (C5H7)
P = cyclopropenyl Nnc = not natural constituent of normal fats.
F* = furanoid
*= Spelling or structure uncertain.
**= Original designation of structure incorrect; more probable structure listed.
Examples: 14:2 = 14 carbon atoms, 2 sites of unsaturation. 9:0 di-acid = HOOC(CH2)7COOH References cited within Table 1 include the following: 1) C. Y. Hopkins (1972), Fatty Acids with Conjugated Unsaturation, in Topics in Lipid Chemistry (F. Gunstone, ed.), Elek Science, London, pp. 37-87; 2) P. G. Robinson (1982), Common Names And Abbreviated Formula For Fatty Acids. J. Lip. Res. 23:1251-1253; 3) G. D. Fasman (1989), Practical Handbook of Biochemistry and Molecular Biology, CRC Press, Boca Raton, Fla., pp. 514-522; 4) F. D. Gunstone, J. L. Harwood and F. B. Padley, The Lipid Handbook (2nd Ed.), Chapman and Hall, London, 1992; and 5) F. D. Gunstone and B. G. Herslof, A Lipid Glossary, The Oily Press, Dundee, first edition 1992, second edition in press.

Hydrophobic Fibers with Dimensional Stability in Wet State

In some applications it is advantageous that the cellulosic fibers be both hydrophobic and not swell excessively in contact with aqueous fluids. This is important in situations in which the final product containing the hydrophobic fibers should have dimensional stability both in dry and wet environment. Improved dimensional stability in wet conditions can be achieved for example by reducing the swelling of the fibers when in contact with moisture. The property of the swelling of the fibers can be measured indirectly by the analysis of their Water Retention Value (WRV). The procedure for measuring WRV is described below in Example 42. A decrease of the WRV of the fibers indicates a reduction in the degree of swelling. According to the invention, one possible way of achieving both hydrophobicity and reduced swelling of the cellulosic fibers is by imparting the hydrophobicity to them by using various methods described in this invention and combining this treatment with cross-lining of the fibers with or without additional cross-linking agents. The cross-linking process can be carried out at various stages of the treatment of the cellulosic fibers. For example it can be applied before the hydrophobic treatment, simultaneously with the hydrophobic treatment or after the hydrophobic treatment. The cross-linking can also be initiated before the hydrophobic treatment and carried out through the hydrophobic treatment process or can proceed during the hydrophobic treatment stage and continue after the hydrophobic treatment has been completed.

Various known cross-linking agents can be used to effectively cross-link cellulosic fibers. For example the use of formaldehyde and various formaldehyde addition products to cross-link cellulosic fibers is known in the art. This approach is described in U.S. Pat. No. 3,224,926 (to Bernardin); U.S. Pat. No. 3,241,553 (to Steiger); U.S. Pat. No. 3,932,209 (to Chatterjee); U.S. Pat. No. 4,035,147 (to Sangenis et al.); and U.S. Pat. No. 3,756,913 (to Wodka). Other references disclose the use of dialdehyde cross-linking agents. See, for example, U.S. Pat. No. 4,689,118 (to Makoui et al.) and U.S. Pat. No. 4,822,453 (to Dean et al.). Dean et al. discloses absorbent structures containing individualized, cross-linked fibers, wherein the cross-linking agent is selected from the group consisting of $C_2$-$C_9$ dialdehydes, with glutaraldehyde being preferred. The use of specific polycarboxylic acids to cross-link cellulosic fibers is also known in the art. See, for example, U.S. Pat. No. 5,137,537 (to Herron et al.), U.S. Pat. No. 5,183,707 (to Herron et al.), and U.S. Pat. No. 5,190,563 (to Herron et al.). The Herron et al. patents disclose absorbent structures containing individualized cellulosic fibers cross-linked with a $C_2$-$C_9$ polycarboxylic acid. The ester cross-link bonds formed by the polycarboxylic acid cross-linking agents are different from the cross-link bonds that result from the mono- and di-aldehyde cross-linking agents, which form acetal cross-linked bonds.

Usually the cross-linking of cellulosic fibers requires a certain amount of energy to be delivered to them in order to accomplish the cross-linking process. This energy can be delivered to the fibers in various forms such as, for example, in the form of heat treatment using various known sources of thermal radiation. For example, applying mechanical pressure to the fibers can also enhance the cross-linking effect. If thermal energy is used, the cross-linking of the fibers can occur even without using additional chemical cross-linking agents. This is probably due to the self-cross-linking reactions, which can undergo within the cellulosic fibers between the functional groups of cellulose. To enhance the effect of the self-cross-linking of cellulose such reactions can be catalyzed by various catalysts such as metal salts, oxides and other metal-containing compounds.

According to the invention, the swelling of cellulosic fibers in wet conditions can also be reduced for instance by imparting hydrophobicity both to the surface of the fibers and to the inside of the fibers. This can be accomplished, for example, by pre-swelling the cellulosic fibers before the hydrophobic treatment in order to facilitate the penetration of the hydrophobic agents inside the fiber. As a result, the obtained, dried fibers become hydrophobic both on the surface and on the inside. This makes them more resistant to swelling in moist conditions thus imparting greater dimensional stability. The pre-swelling of the fibers is possible by using various swelling agents known to effectively swell cellulose. An example of such known treatment is swelling of cellulose in aqueous solution of sodium hydroxide. In this case, the pre-swollen cellulosic fibers can be treated subsequently with a hydrophobic agent to impart hydrophobicity to them. For instance, it can be done by treating the pre-swollen fibers with a polyvalent metal salt to precipitate the polyvalent metal hydroxide within the fibers and on the surface of the fibers and then by applying a soluble salt of fatty acid to the fibers. Without being bound to theory, it is believed that as a result of such a treatment, an insoluble, hydrophobic salt of the polyvalent metal and the fatty acid is formed within and on the surface of the fibers. Various cellulose swelling agents are known and can be used in the present invention.

Treatment of Cellulosic Fibers with Hydrophobic Agents

Another aspect of the invention is hydrophobic cellulosic fibers and a method of imparting hydrophobicity to them by treating the fibers directly with a hydrophobic agent such as a fatty acid or a polyvalent metal salt of a fatty acid at a temperature close or above the melting point of the hydrophobic agent. An example of the hydrophobic agent used in the invention would be aluminum stearate. This compound melts at a temperature of about 110—about 115° C. and can form a coating on the cellulosic fibers thus rendering them hydrophobic.

Yet another aspect of the present invention is hydrophobic cellulosic fibers and a method of imparting hydrophobicity to them by treating the fibers directly with a solution of a water-insoluble hydrophobic agent in a suitable solvent such as various organic solvents.

A hydrophobic agent used for treating the cellulosic fibers can be used as a component of carrier in the form of particles such as other fibers, for example synthetic fibers, which can be blended with the cellulosic fibers and the blend is then cured at a temperature allowing the hydrophobic agent to melt or change into vapor. Without being bound to theory it is believed that the hydrophobic agent in the form of a liquid or vapor can diffuse out of the carrier particles and coat the cellulosic fibers thus rendering them hydrophobic.

When used in the preparation of fibers bound with a polyvalent cation-containing compound and coated thereon a fatty acid containing compound, the fatty acid containing compound desirably is applied in an amount of from about 0.01 part fatty acid containing compound to about 5 parts fatty acid containing compound per 100 parts of treated fiber, which is from about 0.01 weight percent to about 5 weight percent, based on the weight of the treated fiber, more desirably, the fatty acid containing compound is from about 0.01 weight percent to about 3 weight percent, preferably from about 0.05 weight percent to about 1.5 weight percent, more preferably from about 0.1 weight percent to about 1 weight percent.

The fatty acid containing compound may be applied to the fibers in various ways, such as, for example, by spraying the compound which may be heated to increase fluidity, or as a solution or suspension in a liquid, such as water or an organic liquid, or as an aqueous solution of a soluble salt of the fatty acid, such as, for example, an alkali metal salt, preferably a sodium salt.

The addition of filler to the material of the present invention increases barrier performance by partially blocking the pores of the nonwoven web, resulting in improved barrier quality. Filler suitable for use in the practice of this invention include calcium carbonate, various kinds of clay, such as, for example, bentonite and kaolin, silica, alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, mica, carbon, calcium oxide, magnesium oxide, aluminum hydroxide, pulp powder, wood powder, cellulose derivative, polymer particles, chitin and chitin derivatives.

In one embodiment of this invention, a solid material capable of forming physical and/or chemical bonds with a polyvalent metal containing compound is treated in the first step with polyvalent metal-containing compound, and in the second step with a fatty acid containing compound to produce a hydrophobic coating on the solid material. This is accomplished by treating the solid material with a polyvalent metal-containing compound to attach the polyvalent metal to the solid material and then by depositing on it a fatty acid containing compound which is capable of forming ionic an/or coordination bonds with the polyvalent metal.

These two steps can be conducted separately or in a continuous process. The polyvalent metal containing compound can be deposited on the solid material, for example, by spraying in the form of a microdispersion, or by dipping the solid material in a solution or dispersion of the polyvalent metal-containing compound. The polyvalent metal containing compound is deposited on the solid material in its insoluble form and has a general formula of MeA, where Me is the polyvalent metal cation and A is an anionic group. The polyvalent metal can form a physical bond with the solid material or be fixed on the surface through chemical bonds. The fatty acid containing compound can be in the form of a liquid or gaseous microdispersion containing the fatty acid containing compound. The fatty acid containing compound can be used either in a liquid form or in a vapor form.

In the method of the invention, the fatty acid containing compound produces a compound having a general formula of RCOOB, where R is an organic, generally hydrophobic group and COOB is a carboxyl group COOH, where B is a hydrogen atom H, or COOB is a carboxylate group, where B is a monovalent metal. The COOB group is capable of reacting with the MeA compound deposited on the solid surface to yield an insoluble product of the reaction between RCOOB and MeA.

As a result of this reaction, a byproduct BA is formed which can remain on the solid surface or can be removed by washing or by evaporation. In either case, to complete the reaction, after depositing the fatty acid containing compound on the solid material pretreated with the polyvalent metal containing compound, a gas stream may be applied onto the solid material. In the preferred embodiment, A in the MeA compound is a hydroxyl group OH and B in the RCOOB compound is hydrogen H. Then the byproduct of the reaction between MeA and RCOOB is water, which is easily removed by evaporation when applying the gas stream. The gas stream can also facilitate removal of any other volatile compounds such as solvents used in the method of the invention. The scope of the invention includes the hydrophobic solid material obtained, and can be used to obtain natural or artificial fibrous or inorganic materials impermeable to water and to aqueous solutions, and/or absorbing fats or both hydrophobic and lipophobic materials.

The invention provides a solid material which is hydrophobic or lipophilic or both hydrophobic and lipophobic as well as a simple, rapid and low-cost treatment method which can be exploited in practice on the industrial scale.

An object of the invention is to provide a treatment method of which the yield and kinetics are suitable for industrial scale. Another object of the invention is to provide a method which eliminates the use and creation of toxic and corrosive reagents, effluents and residues.

One aspect of the invention provides a treatment method applicable to various solid materials, and, in general, any solid material capable of creating bonds with polyvalent metal containing compounds. Another aspect of the invention enables various materials to be treated, such as cellulose and other materials, including natural and synthetic organic polymers in the form of fibers, paper, nonwovens and textiles, as well as inorganic materials, such as glass. Suitable polymers include for example polyamides such as nylon 6 or nylon 66, polyesters such as poly(ethylene terephthalate), poly(oxyethylene), poly(vinyl alcohol), chitosan, chitin, starch, and collagen.

The invention concerns a method for treating a solid material to deposit a polyvalent metal ion containing compound MeA on the solid material. In one embodiment the MeA reacts with reactive functional groups of the solid material to form a physical and/or chemical bond such as a covalent, coordination and/or ionic bond. Thus, the polyvalent metal cation is bound to the surface of the solid material. In the second step a bond is created between the polyvalent metal ion containing compound and fatty acid containing compound, wherein a fatty acid containing compound ROOB is used, where B is hydrogen H or monovalent metal and R is an organic, generally hydrophobic group, ROOB being selected so that it can react with the polyvalent metal containing compound MeA deposited on the solid material, to produce a chemical bond, generally coordination and/or ionic bond, with ROOB with formation of a byproduct in the form of the BA salt or water, where the latter can be evaporated under the reaction conditions. A liquid or gaseous microdispersion is produced of a composition containing a fatty acid containing compound and applied on the solid material with deposited MeA, and a gas stream, which is neutral to the reaction of ROOB with MeA deposited on the solid material, is applied to facilitate the distribution and diffusion of ROOB to the parts of the solid material with deposited MeA accessible to the gas stream and to facilitate the removal of any volatile byproducts.

The solid material may contain reactive functional groups, which enable the formation of physical and/or a chemical bonds with the polyvalent metal containing compound. If the solid material is a structure composed of fibers such as cellulosic fibers then the first stage of the treatment may be accomplished by treating the fibers with a polyvalent metal containing compound and then making the structure constituting the solid material. Thus, the solid material produced will contain on its surface a polyvalent metal containing compound.

As used herein, the term "microdispersion" means a dispersion of liquid droplets having a mean diameter equal to or less than $1 \times 10^{-6}$ meter (1 micron). A microdispersion according to the invention may be produced on at least part of at least one first free outer face of the solid material simply by contacting the material with the microdispersion, for example, either by spraying directed onto this first free outer face of the solid material, or by application of a solid support loaded with the liquid composition in contact with this first face, or by wetting, for example, by immersion in a bath of the liquid composition containing a volatile solvent, followed by evaporation of this volatile solvent.

A quantity of liquid composition containing fatty acid containing compound is applied in contact with at least one first free outer face of the solid material. A gas stream is then applied to at least one free outer face of the solid material, which may be the same first face or another face. The microdispersion is preferably deposited on the solid material before applying the gas stream to the solid material. Alternatively, the gas stream can also be applied to the solid material at the same time as a microdispersion is deposited thereon. In this case, care should be taken to prevent vaporization of the liquid composition before it comes into contact with the solid material.

In a preferred method, a microdispersion of at least one liquid composition including a fatty acid containing compound is deposited by spraying directed towards the solid material, for example, with a nozzle directed towards one face of the solid material. Alternatively, deposition can be accomplished by contact of the material with a solid support previously loaded with a liquid composition mainly consisting of a fatty acid containing compound in the liquid state and/or by wetting the solid material with a liquid composition formed of a solution of the fatty acid containing compound in a neutral volatile solvent. The solid support loaded with liquid composition may be chosen from an absorbent pad applied to the solid material, for example, a pad of the felt type, a non-absorbent pad, for example of the dating pad type, an absorbent or non-absorbent roller driven in rotation by rolling on the first face of the solid material, for example, of a paint roller or printing machine inking cylinder type, or a brush or the equivalent.

In order to wet the solid material, it may be immersed in a bath of the liquid composition. As soon as it leaves the bath, the neutral volatile solvent evaporates, leaving in place microdroplets of the fatty acid containing compound dispersed on the solid material.

The liquid composition may also incorporate a solvent, in particular, a volatile neutral solvent. If a fatty acid containing compound is soluble in polar solvents such as in the case of a fatty acid salt of a monovalent metal, the volatile solvent is for example water or the solvent is chosen from the group formed of polar organic solvents such as water, alcohols, ketones, etc. On the other hand, if a fatty acid containing compound is soluble in nonpolar solvents as in the case of a long-chain fatty acid in its neutral form, then the volatile solvent can be chosen for example from the group formed of petroleum ethers, low molecular weight alkyl esters, such as ethyl acetate, or chlorinated solvents such as chloroform, trichloroethylene, etc. If a fatty acid containing compound is a liquid, it may not be necessary to use a solvent.

The gas stream is applied continuously and a gas flow coming from the solid material is evacuated so as to prevent any recirculation onto the solid material. The gas flow coming continuously from the solid material makes it possible in particular to evacuate continuously the volatile compounds. For example, when the fatty acid containing compound is a fatty acid in its neutral form and the polyvalent metal containing compound is a hydroxide of the polyvalent metal, the volatile byproduct of the reaction is water.

In one embodiment of the invention, the stream of gas is directed towards the surface of the solid material with a positive velocity component perpendicular to the surface of the solid material.

It should be noted in particular that, unlike former vapor phase treatment methods involving the use of fatty acid chlorides as disclosed in U.S. Pat. No. 6,342,268, in the method of this invention, both the reagents and the by products are neutral, non-toxic and non-corrosive.

A function of the gas stream applied to the solid material has the function of bringing about entrainment of the fatty acid containing compound initially placed in microdispersed form in the liquid state on the solid material on sites occupied with the polyvalent metal containing compound, and of removing any excess. It has the function of enabling the reaction between the polyvalent metal containing compound and the fatty acid containing compound to take place of entraining any volatile byproducts formed by the reaction. It has the function of driving the kinetics of the reaction forward by removing volatile byproducts.

As an example, a reaction between a solid material having on its surface polyvalent metal containing compound attached in the form of polyvalent metal hydroxide MeOH and a fatty acid RCOOH, may be written according to the following equation (I):

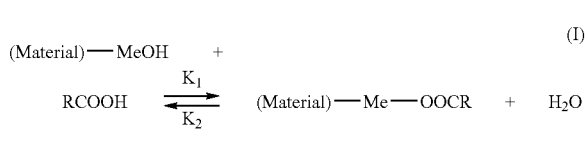

where $K_1$ and $K_2$ are velocity constants in the direction of formation and dissociation respectively. The rate of reaction may be written according to the following equation (II):

$$V=K_1[(\text{Material})\text{-MeOH}][\text{RCOOH}]-K_2[(\text{Material})\text{-Me}\text{—OOCR}][H_2O] \quad (II).$$

R is, for example, an organic group containing more than 6 carbons, in particular between 8 and 50 carbons, is in general hydrophobic. R may be chosen from the family of aliphatic or aromatic radicals derived from fatty acids containing more than 10 carbons and in particular between 14 and 50 carbons. R may or may not contain one or more hetero-atoms, and may be saturated or unsaturated. For example, R may be a perfluorinated alkyl group, the hydrophobic character of which is much more marked than the perhydrogenated alkyl group of the same carbon skeleton. R may also incorporate functions such as hydroxyl, amine or amide functions making it possible to attach the fatty acid containing compound to polyvalent metal containing compound deposited on the solid material in the first stage of the treatment. R can be from any of the previously named fatty acids, without the carboxyl group, of course. Examples of some very desirable fatty acids are hydroxy acids, such as, for example, glycolic, lactic, malic, citric, tartaric, hyaluronic, alginic, salicylic, 2-hydroxylinoleic, cerebranic, hydroxynervonic, 10-hydroxydecanoic, hydroxyallenic, ricinoleic, lesquerolic, densipolic, auricolic, beta-dimorphecolic; sulphur-containing acids dodeca thia acetic, tetradeca thia acetic; methoxy acids, such as, for example, 2-methoxy-5-hexadecanoic, methoxytetradecanoic, methoxypentadecanoic, methoxyoctadecanoic; keto acids, such as, for example, 9-keto-decanoic; amino acids, such as, for example, alanine, beta-alanine arginine, asparagine aspartic acid, carnitine, citrulline, cysteine, cystine, gamma-aminobutyric acid, glutamic acid, glutamine, glutathione, glycine, histidine, hydroxyproline, isoleucine, leucine, lysine, methionine, ornithine, phenylalanine, proline, serine, taurine, threonine, tryptophan, tyrosine, valine; and halogenated acids, such as, for example, p-chlorophenoxyisobutyric acid, perfluoro-n-decanoic acid, perfluoro-n-octanoic acid, and perflorooctane sulfonic acid.

The solid material desirably has reactive groups such as alcohol (—OH), amino (—$NH_2$) and mercapto (—SH), such as, for example, polyamides such as nylon 6 or nylon 66, polyesters such as poly(ethylene terephthalate), poly(oxyethylene), poly(vinyl alcohol), chitosan, chitin, starch, and collagen. The solid material is preferably a cellulosic material in the form of nonwoven, paper, film, textile, natural or artificial fibres, and wood, etc.

The solid material can be made also of glass or silica or other solid inorganic or organic material capable of forming physical or chemical bonds with polyvalent metal containing compounds.

In a preferred embodiment of this invention, treatment according to the invention makes it possible to obtain a solid hydrophobic material. In various alternatives it is possible to provide the solid material with other properties according to the characteristics of the groups R. Accordingly, it is possible to choose hydrophobic groups R which may have in addition other properties, in particular which may be oleophobic if the group R is a perfluorinated organic group, and which are protectors against ultra violet rays and/or absorb ultraviolet rays, colored rays etc. Useful in the practice of this embodiment of this invention are acids with perfluorinated organic groups, such as, for example, perfluoro-n-decanoic acid, perfluoro-n-octanoic acid, perflorooctane sulfonic acid; and acids with uv absorbing groups, such as, for example, acids containing chromophore aromatic groups such as salicylic acid, aminobenzoic acid, carminic acid.

At the start, the reaction proceeds with a high velocity since there is no negative contribution from the second term of the expression. In a closed system, this rate however may decrease with the increase in concentration of (Material)-Me —OOCR and of $H_2O$. In an open system the reaction can be easily completed by removing $H_2O$, for example, by evaporation.

In one example of the prior art, the attachment of fatty acid acyl groups to the solid material was achieved in the vapor phase by using fatty acid chlorides. Such compounds are sensitive to moisture, produce strong odor and are toxic. The byproduct of the reaction of fatty acid chlorides with the protogenic groups of the solid material is hydrogen chloride, which is very toxic and corrosive.

The solid material with attached polyvalent metal containing compound is placed in a treatment space adapted so as to minimize, or even prevent, according to the characteristics of the gas stream, any return onto the solid material of the gas flow coming from the solid material. If the solid material is non-porous or only slightly porous, the treatment space should be sufficiently large in the transverse direction with respect to the incident gas stream so that the gas flow can be evacuated without being recirculated to the solid material. The side walls of the treatment space surrounding the solid material must not come into contact with the solid material in the transverse direction.

If it is perfectly porous, the solid material with attached polyvalent metal containing compound may be placed in a treatment space which is smaller in the transverse direction, and of substantially the same transverse size as the solid material. However, application of the gas stream and evacuation of the gas flow coming from the solid material is then carried out in open circuit.

Whether the solid material is porous or non-porous, the solid material with attached polyvalent metal containing compound is placed in a treatment space adapted according to the characteristics of the gas stream so that the quantity of gas flow coming from the solid material which can once again be brought onto the solid material by the gas stream is zero or negligible. Optionally, the solid material is placed in a ventilated oven or in an open atmosphere under an extraction hood evacuating the gas flow to the outside. The treatment space is adapted so that, if the treatment space is sufficiently large, the volatile solvents are extracted by dilution from the solid material as it is formed, and/or is extracted by forced evacuation. Desirably, the treatment space is not hermetically sealed but is open and may be put into operation with fresh air in an open atmosphere. Gases useful in the practice of this embodiment of the invention are inert under the conditions used and include, for example, air, nitrogen, helium, carbon dioxide.

It is possible, in a variant of the operating method of the invention, to apply a gas stream and a stream of a microdispersion of fatty acid containing compound simultaneously in the form of a spray directed onto at least one free outer face of the solid material. In this case, the gas stream contains the microdispersion of fatty acid in the liquid state, and it is desirable that the temperature of the gas stream should be as low as possible so as to prevent any vaporization of the fatty acid containing compound before arrival on the solid material. However, it is then advantageous to provide a subsequent step during which a gas stream free from the fatty acid containing compound is applied at a higher temperature in order to encourage the treatment.

The method according to the invention may be carried out with ambient air and with a material which is not previously dried. The gas stream may thus be quite simply atmospheric air or dry air. It is also possible to use any other neutral gas, for example pure nitrogen or carbon dioxide, to prevent the oxidation of the material or of the reagent.

The physical characteristics of the gas stream velocity, flow rate, temperature, pressure, dimensions are adapted in relation to the solid material to be treated and the operating conditions selected. In particular, a gas stream is chosen having a sufficiently low velocity so that the dwell time of the fatty acid containing compound on the material at the chosen reaction temperature is sufficiently long to allow time to react with all the sites of the solid material with polyvalent metal containing compound attached to it.

The gas stream may be formed by any appropriate means, for example with the aid of one or more fans positioned so as to operate in compression and/or in extraction.

In FIG. 8, a sample of solid material such as a glass plate, a piece of paper or other material, pretreated with polyvalent metal containing compound, is placed under a rotating fan 2 directing a gas stream 3, for example formed of atmospheric air at ambient temperature, onto a free outer face 4 of the sample 1, on which a microdispersion 5 has already been formed of a liquid composition of a fatty acid containing compound for example by means of an absorbent pad impregnated with a liquid composition applied with pressure onto the face 4. The gas flow 6 coming from the sample 1 is formed of the reflected flow 6a and the flow 6b having passed through the sample 1 if the latter is porous. These flows 6a, 6b are evacuated either to the open air as shown or into an extraction hood if the assembly is placed under a hood. If the sample 1 is porous, it is treated throughout all its thickness. If it is not porous, only its face 4 is treated.

FIG. 9 illustrates a continuous method for producing a strip 9 of solid material such as printing paper with attached polyvalent metal containing compound, in which a spray nozzle 10 is used to spray the liquid composition of a fatty acid containing compound onto the part 11 of the free outer face 12 of the strip 9 which passes in the gas stream 3 formed by the fan 2. Preferably, the spray nozzle 10 is inclined countercurrently to the direction of movement of the strip 9 under the fan 2.

As a variant, not shown, the nozzle 10 could also be placed upstream to the gas stream 3 with respect to the direction of movement of the strip 9. The treatment then comprises two successive stations: a spraying station followed by a station for applying the gas stream 3.

In the variant of FIG. 10, a blower 13 is used, which may be provided with means for heating the gas stream 15. The sample 18 has been previously wetted with a liquid composition of fatty acid containing compound contained in a vessel 19 by simply soaking it instantaneously in the bath of the vessel 19. The sample 18 is placed under an extraction hood 20.

This variant may be used with a porous sample 18, which is then treated throughout its thickness. Several blowers 13 may be used to treat each large face of the sample 18.

The variant of FIG. 10 may also be used with a non-porous sample, the liquid composition being formed of a highly diluted solution of fatty acid containing compound in a neutral volatile solvent evaporated by the gas stream, or before applying the gas stream, so as to leave only a microdispersion on the surface.

The method according to the invention has many advantages compared with the prior art, and in particular rapid reaction times make it possible to work at relatively high temperatures and the material, polyvalent metal containing compound and fatty acid containing compound are indeed only subjected to these high temperatures for a very short time; no harmful reaction substrates such as fatty acid chlorides or byproducts, such as gaseous halogenated acids, are produced during the treatment; the reaction can take place without any solvent or catalyst, and generates products which do not present any safety or environmental problems; and the reaction may be carried out with many commercial reagents, which are for the greater part low in cost.

In general, the treated material does not require any washing or subsequent treatment. The method is very simple and does not require the use of strictly anhydrous conditions or an inert atmosphere, or a confinement chamber, and in most cases, the ambient air may be used as the carrier gas, and the solid material may be used without previous drying. It is possible to treat large areas of solid material easily in situ, whether continuously or not. The invention may thus make it possible to obtain a solid material containing on all its specific area accessible to the gases, and solely on this surface, hydrophobic groups, which can include between 8 and 50 carbons.

The invention applies in this respect to very many different solid materials. Accordingly, a solid material according to the invention may be:

a solid material permeable to gases, the method according to the invention not affecting the gas permeability property of the material;

a solid biodegradable material, the method according to the invention not affecting the biodegradability properties of the material;

a colored solid material, the method according to the invention not affecting the color of the material;

a solid material essentially formed of crosslinked polymeric macromolecular material(s), when sufficient durability of the hydrophobic character is desired, or non-crosslinked polymeric macromolecular material(s), if durability is not desired or on the other hand if low durability is desired;

a solid material essentially formed of cellulosic materials;

a solid material formed of a natural or artificial fibrous structure being in the form of a sheet or divided form in particular paper, a wood-based structure, or a textile structure, impermeable to water and to aqueous solutions and/or absorbing fats; and a solid material formed of a porous or non-porous inorganic structure, in particular glass or silica.

It should also be noted that the solid material according to the invention may be porous or fibrous, but it is not necessarily porous or fibrous. In particular, the solid material according to the invention may also be made of glass, as a sheet, plate, block or as glass wool, or of silica. In the case of glass, glass is obtained with a hydrophobic outer face which does not retain water.

The invention may be the subject of very many other practical applications. A cellulosic fibrous structure according to the invention may accordingly for example serve to provide undergarments, towels or protective cloth.

In addition, it may serve to provide dressings impermeable to water and to aqueous solutions and permeable to gases. Such a dressing is particularly effective in as much as it prevents any bacterial contamination by aqueous solutions and facilitates healing, taking into contact its gas penneability properties.

The invention makes it also possible to obtain, in an alternative manner to previously known waterproofing methods, clothing, which is impermeable to water, and, the invention makes it possible to obtain textile structures impermeable to water and permeable to air.

The invention also makes it possible to obtain a hydrophobic paper permeable to gases, which may or may not be biodegradable and which may or may not be colored. Such a paper may be the subject of very many applications, and in particular for packagings impermeable to water and aqueous solutions and permeable to air, or for a package or bag impermeable to water and to aqueous solutions, which is biodegradable.

The invention is applicable to printing paper. Printing paper commonly used in printers, photocopiers, and in printing works and for writing must have a partially hydrophobic character. The purpose of this is to permit the diffusion of water-based inks into the texture of the paper but in a controlled manner so that the ink does not spread out as may be observed for example on blotting paper. This partially hydrophobic character is obtained in the prior art by adding hydrophobic additives such as alkyl ketene dimers, long chain derivatives of succinic anhydride or compounds of the rosin family. All these compounds are added to the cellulose in aqueous suspension, which presents considerable technical problems taking into account the strongly hydrophobic and water insoluble character of these additives. It is thus desirable to have available a method which will enable this partially hydrophobic character to be provided with a method not requiring the use of an aqueous suspension. This partially hydrophobic character may be provided by a method according to the invention using small quantities of grafting reagents.

In addition, since a solid material according to the invention is hydrophobic, it is in general also lipophilic. Accordingly, the solid material according to the invention may be applied in all cases where fat absorption properties are desired.

The invention provides a solid composition, which may be in divided form for absorbing hydrocarbons which has a density less than that of water, for example, a hydrophobic wood chip or sawdust composition absorbing hydrocarbons and oils and capable of floating on the surface of water. Such a composition may serve in particular for the treatment of water pollution by hydrocarbons.

The invention also concerns a treatment method and a solid material wherein all or part of the characteristics mentioned above and hereinafter are combined.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, the term can mean within an order of magnitude, preferably within 5-fold, and more preferably within 2-fold, of a value.

EXAMPLES

The following Examples illustrate the invention, but are not limiting.

Example 1

Production of Handsheet Web#1

Materials

1. CARESSA® 1100 available from Buckeye Technologies Inc. of Memphis, Tenn. CARESSA® 1100 is a type of chemically treated cellulose fiber, which was originally developed for use in absorbent structures and is described in U.S. Pat. No. 6,562,743 and a published counterpart, WO 00/38607, both of which are hereby incorporated by reference in their entirety. CARESSA® 1100 is also referred to as SW or SW-16. In the preparation of CARESSA® 1100, which is based on FOLEY FLUFFS®, aluminum sulfate is added to a slurry of cellulose fibers and the pH is adjusted so that aluminum hydroxide is precipitated on the fibers. The preparation is completed by the addition of citric acid.
2. CARESSA® 3100 available from Buckeye Technologies Inc. of Memphis, Tenn. CARESSA® 3100 is a type of chemically treated cellulose fiber, which was originally developed for use in absorbent structures and is described in U.S. Pat. No. 6,562,743 and a published counterpart, WO 00/38607, both of which are hereby incorporated by reference in their entirety. CARESSA® 3100 is also referred to as SW-25. In the preparation of CARESSA® 3100, which is based on FOLEY FLUFFS®, aluminum sulfate is added to a slurry of cellulose fibers and the pH is adjusted so that aluminum hydroxide is precipitated on the fibers. The preparation is completed by the addition of an aqueous mixture of sodium hypophosphite and aluminum sulfate.
3. HPF™ is a mercerized cellulose fiber available from Buckeye Technologies Inc. of Memphis, Tenn.
4. FOLEY FLUFFS® is cellulose fluff pulp available from Buckeye Technologies Inc. of Memphis, Tenn.
5. FFLE™ and FFLE+™ based on FOLEY FLUFFS® and has added thereto aluminum sulfate as a debonding agent to lower the disintegration energy of the comminution sheet. This is described in U.S. Pat. No. 6,159,335, which is hereby incorporated by reference herein in its entirety.
6. RB265-30W (merge #4591, 30 gsm) is a wettable synthetic polypropylene nonwoven carrier from American Nonwovens Corporation, Columbus, Mich.
7. Polyester fiber from Kosa, Salisbury, N.C. merge #35379A, 6.7 dtex, 4 mm.
8. Bicomponent AL Delta binder fiber, 6.7 dtex, 6 mm, with a polypropylene core and polyethylene sheath from FiberVisions a/s, Varde, Denmark.
9. Trevira bicomponent binder fiber, merge #1663, 2.0 dtex, 3 mm, is a fiber with a polyester core and a polyethylene sheath from Trevira Neckelmann a/s, Silkeborg, Denmark.
10. Tylac-NW-4036-51B is an emulsion of a styrene-butadiene terpolymer from Dow Reichhold, Durham, N.C.
11. Artilene blue pigment 6825-9 paste from Clariant Corp., Charlotte, N.C.
12. 18 gsm cellulose tissue (Cellutissue 3024) is supplied by Cellu Tissue Holdings, Inc., East Hartford, Conn.
13. ND416 cellulose fluff (Weyerhaeuser Co., Tacoma, Wash.).
14. Polyester fiber (Kosa, merge #35379A).
15. AF 192 is an emulsion of an ethyl vinyl acetate copolymer from Air Products and Chemicals, Inc., Allentown, Pa.
16. EP 1188 is an emulsion of a vinyl acetate copolymer from Air Products and Chemicals, Inc., Allentown, Pa.
17. Coverstock material 22 gsm is a through-air-bonded carded web supplied from Sandler AG, Schwarzenbach/Saale, Germany.

Methods

Handsheets of Web #1 were produced on a laboratory airlaid forming device by depositing the following layers on a wettable synthetic nonwoven carrier RB265-30W, merge #4591, 30 gsm, from American Nonwovens Corporation, Columbus, Mich.:

Layer 1: Blend of 14.7 gsm polyester fiber (Kosa, merge #35379A, 6.7 dtex, 4 mm) and 30.3 gsm bicomponent AL Delta binder fiber (6.7 dtex, 6 mm) from FiberVisions a/s, Varde, Denmark.

Layer 2: Blend of 34.7 gsm mercerized cellulose fiber (Buckeye, HPF) and 3.5 gsm Trevira bicomponent binder fiber (merge #1663, 2.0 dtex, 3 mm), from Trevira Neckelmann a/s, Silkeborg, Denmark.

Layer 3: Blend of 38.1 gsm cellulose fluff (Buckeye, Foley Fluffs) and 3.5 gsm Trevira bicomponent binder fiber (merge #1663).

The sheets were pressed slightly and cured in the lab convection oven at 150° C. for 15 minutes. The density of the sheets was 0.035 g/cm$^3$.

Example 2

Coating Handsheet Surfaces

The surface of some of the handsheets produced following the procedure described in Example 1 was coated on the carrier side with a foam having the following formulation: 10% solids content of Tylac-NW-4036-51B from Reichhold plus 0.52% of latex solids content of Artilene blue pigment 6825-9 paste from Clariant Corp., Charlotte, N.C. The blue foam was applied in stripes similar to those shown in FIG. 1A. The width of each stripe was 5 mm and a space between each pair of adjacent stripes was also 5 mm. The handsheets were cured in the lab convection oven at 140° C. for 5 minutes. The samples were designated as Web #2 and had a density of 0.040 g/cm$^3$.

Example 3

Demonstration of Wettable Zones

In FIG. 1A, one example of this invention is shown which is web #2. The surface of web #2 comprises one or more regions of more wettable zones through which body fluid or its stimulant can flow easily for efficient fluid intake, and less wettable zones through which the flow of the liquid is reduced or the liquid does not penetrate. These zones are designed for reduced flow back to the surface and lower rewet.

The more wettable zones are understood here as zones, which can be wetted relatively easily with a liquid to be absorbed. The less wettable zones are zones, which are not wetted as easily with the liquid, in this example the blue stripes of hydrophobic latex. In other words, the contact angle between the liquid and the surface of a more wettable zone will be lower than the contact angle between the liquid and the less wettable zone. As a result the liquid will tend to run on the surface of the structure from a less wettable zone toward a more wettable zone as soon as it gets in contact with such a more wettable zone. The effect of this controlled wetting is that the surface of the less wettable zones will remain drier than the surface of the more wettable zones. This will create a visual effect of improved stain hiding and dryness of the surface of the structure. Optionally, the different zones can be made more visible to the consumer, for example, by using different colors for more wettable and for less wettable zones, creation of various shapes or texture of these zones or by other techniques.

Figure 1C:
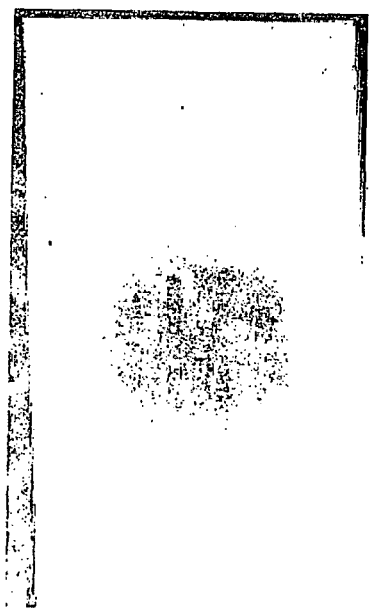

The effect described above is illustrated in FIG. 1A, where the more wettable zones are white stripes whereas the less wettable zones are blue stripes. The colors of the more wettable and less wettable zones, their shape and pattern may vary depending on consumer preference and on the creativity of the manufacturer. Another example is shown in FIG. 1C, in which the sample was made as web #2 in Example 2, but without the blue pigment.

Example 4

Formation of Handsheet Web#3

Figure 2:
FIG. 2 represents a handsheet designated Web#3 with a profiled forming screen having protrusion patterns as reflected in the material produced.

Handsheets of Web #3 were produced on a laboratory airlaid forming device with a profiled forming screen having a pattern as reflected in the material produced with it shown in FIG. 2. The protrusions P had each a diameter of 3 mm in diameter and a height of 2 mm. The distance between the axes of adjacent protrusions was 5 mm.

Profiled forming screens of this type and associated techniques for the production of materials using them are disclosed in U.S. Ser. No. 60/493,875 filed Aug. 8, 2003, which is hereby incorporated by reference herein in its entirety.

The following layers of fibers were deposited on the forming screen:
Layer 1: Blend of 18.1 gsm polyester fiber (Kosa, merge #35379A) and 37.3 gsm bicomponent AL Delta binder fiber (6.7 dtex, 6 mm).
Layer 2: Blend of 42.7 gsm mercerized cellulose fiber (Buckeye, HPF) and 4.3 gsm Trevira bicomponent binder fiber (merge #1663).
Layer 3: Blend of 38.1 gsm cellulose fluff (Buckeye, Foley Fluffs) and 3.5 gsm Trevira bicomponent binder fiber (merge #1663).

The sheets were pressed slightly and cured in the lab convection oven at 150° C. for 15 minutes. The density of the sheets was 0.038 g/cm$^3$.

Example 5

Coating of Synthetic-Sided Handsheets

The surface of some of the handsheets produced following the procedure described in Example 4 was coated on the synthetic fiber side with an aqueous foam containing the following ingredients: 10% solids content of Tylac-NW-4036-51B from Reichhold plus 0.52% of latex solids content of Artilene blue pigment 6825-9 paste from Clariant Corp., Charlotte, N.C.

The foam was applied onto the top surface of the web leaving the indentations uncoated as illustrated in FIG. 3A. The handsheets were cured in the lab convection oven at 140° C. for 5 minutes. The obtained samples were designated as Web #4 and had a density of 0.039 g/cm$^3$.

Example 6

Production of Handsheets

Handsheets of Web #5 were made in a way similar to that used for making Web #3 except for the type of the forming screen used. The forming screen used to prepare Web #5 was a regular, flat screen. As a result the surface of Web #5 was flat. The density of the samples of Web #5 was 0.036 g/cm$^3$.

FIG. 3A illustrates another example of more wettable and less wettable zones, where the less wettable zones were obtained by treating parts of the surface with a hydrophobic polymer containing a blue pigment. In this example the surface is not flat but textured and the zones coated with the hydrophobic polymer are higher than the uncoated, more wettable zones. The red liquid stain is hidden better behind the less wettable zones. The control material in FIG. 3B does not have textured surface and was produced in such a way that its surface had uniform wettability.

Figure 4A:
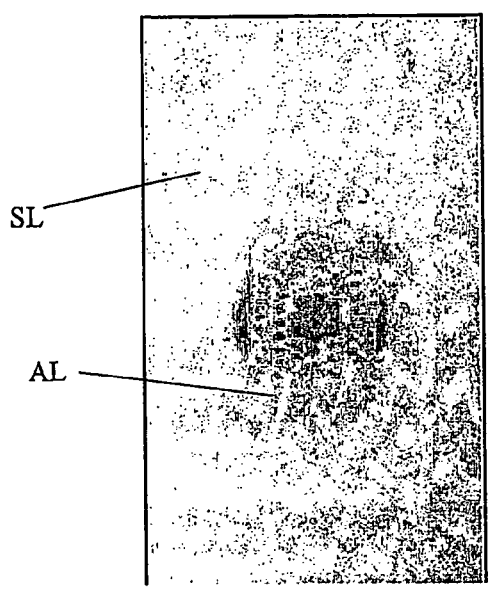
FIG. 4A illustrates an example of the structure of the invention, which is composed of an upper acquisition layer (AL) and a bottom storage layer (SL).

FIG. 4A illustrates an example of the structure of the invention, which is composed of an upper acquisition layer (AL) and a bottom storage layer (SL). Handsheets of a storage layer (SL) were prepared on a laboratory forming device by using 18 gsm cellulose tissue (Cellutissue 3024) and depositing on it a blend of 414 gsm ND416 cellulose fluff (Weyerhaeuser Co., Tacoma, Wash.), and 46 gsm Trevira bicomponent fiber (merge #1663). The web was pressed and cured in the lab oven at 150° C. for 15 minutes. The final density of the sheets was 0.15 g/cm$^3$.

Figure 4B:
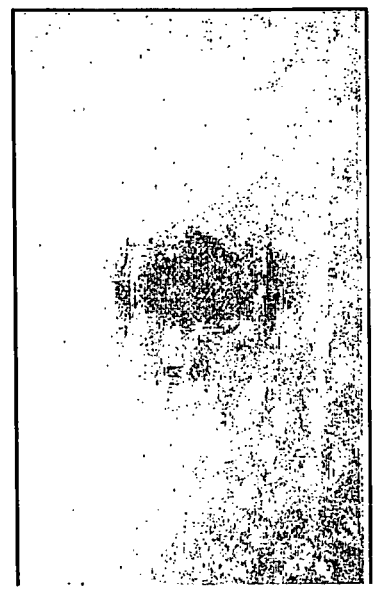
FIG. 4B illustrates a structure comprising an upper layer having flat surface and being wettable on its whole area.

The upper acquisition layer (AL) was made on a lab equipment by depositing 102 gsm CARESSA 3100® fiber blended with 18 gsm Trevira bicomponent fiber (merge #1663) on the forming screen with protrusions described in Example 4. The web was pressed and cured in the lab oven at 150° C. for 15 minutes. The final density of the acquisition layer (AL) was 0.055 g/cm$^3$. The chromatographic analysis of the finish on the bicomponent fibers, as received from the supplier of those fibers, revealed that the finish contained methyl oleate. It is hypothesized that during the curing process of the acquisition layer (AL) methyl oleate reacted with Al ions in the CARESSA 3100® rendering the surface of the acquisition layer (AL) hydrophobic. In the structure shown in FIG. 4A, the upper acquisition layer (AL) is in close contact with the hydrophilic storage layer (SL) at the indentations of the acquisition layer (AL) structure. Thus, the liquid can penetrate easily through these indentations. On the other hand, the protrusions of the acquisition layer (AL) are farther from the hydrophilic storage layer (SL) and therefore they produce the desired stain masking effect due to their hydrophobic surface. The photograph in FIG. 4A shows the effect of stain hiding produced by the acquisition layer (AL). FIG. 4B is a photograph of a structure comprising an upper layer having flat surface and being wettable on its whole area.

Example 7

Testing Rewet Characteristics

Figure 5A:
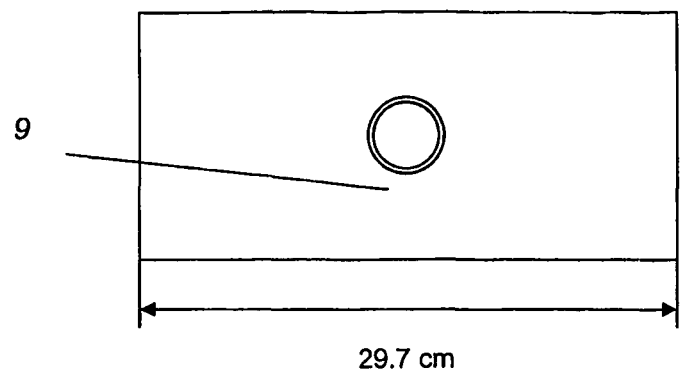
FIGS. 5A and 5B illustrate a top FIT board.
Figure 5B:
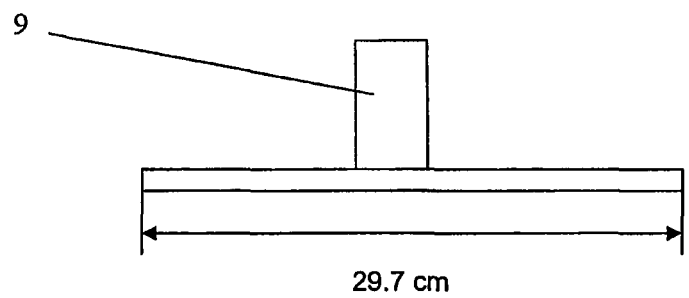

The following procedure was applied to test the rewet characteristics of various samples: An apparatus called Fluid Intake Tester (FIT) was used to test the experimental samples. The FIT consists of a top and a bottom board, which are made of a transparent plastic material such as lexar or plexiglass. The opening diameter for the dose intake tube is 25 mm. The upper plate weighs 872 g. The top FIT board is illustrated in FIGS. 5A and 5B. FIG. 5A is an image of the top view, and FIG. 5B is an image of the side view of the board. The end of the inlet tube (9) is flush with the bottom of the top FIT board. The lower FIT board should be a flat rectangular piece of clear plastic with dimensions similar to the dimensions of the upper board contour. The length of the upper board was 29.7 cm, its width was 19 cm and its thickness was 1.2 cm. The inlet tube (9) was fixed in the center of the top board. The total height of the tube (9) was 6 cm.

Figure 6:
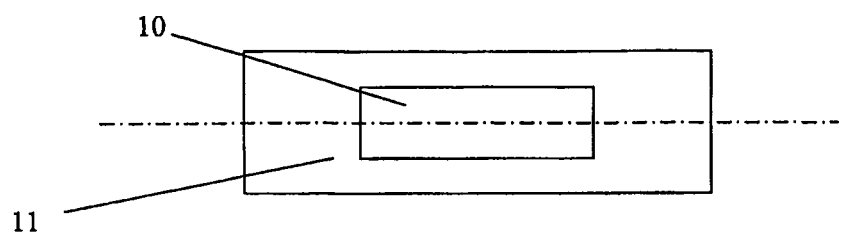
FIG. 6 illustrates the alignment of the tested sample (10) and the storage layer (11).

Each tested sample had dimensions of 70 mm in width and 200 mm in length. It was placed on a storage layer made as described in Example 3. The width of the storage layer was 35 mm and its length was 100 mm. The tested sample (10) and the storage layer (11) were aligned as shown in FIG. 6. The test sample and the storage layer were then covered with a coverstock material, a through-air bonded carded web having basis weight of 22 gsm from Sandler AG, and the whole system was placed between the bottom and the upper FIT boards. Each tested sample system was then insulted through the inlet tube with 10 cm$^3$ of synthetic menses stock solution. This was an aqueous solution containing 0.38% red dye Biebrich Scarlet, obtained from Sigma, Catalogue No. B-6008, 0.9% sodium chloride and 11.8% polyvinylpyrrolidone (PVP) having molecular weight of 55,000 and viscosity in a range of 9.0 cP to 10.0 cP. After waiting for 20 minutes approximately 45 g of pre-weighed Buckeye grade S-22, a 22 gsm cellulose blotter paper, available from Buckeye Technologies, cut to 10.2 cm by 214.1 cm was placed on top of the sample for 2 minutes under load of 2.8 kPa. The load was composed of a spongy solid foam layer to ensure uniform pressure over the whole area of the sample and of a weight. After 2 minutes, the load was removed and the blotter paper was weighed. The difference in weight of the blotter paper before and after the test is the rewet value.

The results of the tests are presented in Table 2. The data indicate that the dryness of Web #2 was better, with a lower rewet, than the dryness of the control Web #1, which had a higher rewet. The results show that Web #4 had the best dryness in the rewet test and the control Web #5 had higher rewet than both Web #3 and Web #4.

TABLE 2

| Sample Web Number | Rewet, g |
| --- | --- |
| 1 | 1.03 |
| 2 | 0.70 |
| 3 | 050 |
| 4 | 040 |
| 5 | 063 |

Example 8

Production of Handsheet Web#6

Handsheets of Web #6 were produced on a laboratory airlaid forming device by depositing the following layers:
Layer 1: Blend of 27 gsm SW16 cellulosic fiber (Buckeye) and 8.5 gsm Trevira bicomponent binder fiber (merge #1663).
Layer 2: Blend of 35 gsm FOLEY FLUFFS® cellulosic fiber (Buckeye) and 2 gsm Trevira bicomponent binder fiber (merge #1663).
Layer 3: Blend of 8 gsm SW16 cellulosic fiber (Buckeye) and 2 gsm Trevira bicomponent binder fiber (merge #1663).

The web was pressed to a thickness of 0.8 mm. It was then sprayed with 1.5 gsm (by solids weight) of AF 192 binder (Air Products) on the surface of Layer 3 and sprayed with 1.5 gsm (by solids weight) of EP1188 binder on the surface of Layer 1. The sheet was cured in the lab convection oven at 150° C. for 15 minutes. The sheet of web #6 had a wettable surface on the side of Layer 3 and a hydrophobic surface on the side of Layer 1.

One milliliter of the synthetic menses stock solution described in Example 7 was poured on the wettable surface of web #6. The structure acquired the liquid, which then became contained in the web and did not penetrate through the opposite, hydrophobic side. The liquid stain was also less visible on the hydrophobic side than on the hydrophilic, wettable side.

The stain masking effect was due to the hydrophobicity of Layer 1 and the hydrophobic nature of the EP1188 binder applied on the outer surface of this layer. It is hypothesized that the presence of Al ions in SW16 fiber and methyl oleate in the formulation of the finish of the bicomponent binder fiber were responsible for the hydrophobicity of Layer 1. As explained earlier, this hydrophobicity was probably due to the reaction between the Al ions and methyl oleate of the finish in the bicomponent fibers during the curing stage. Layer 3 contained significantly lower content of bicomponent fiber and the amount of finish containing methyl oleate was not sufficient to produce the hydrophobic effect with the Al ions on the SW16 fibers.

Example 9

Production of Handsheet Web#7

Handsheets of Web #7 were produced on a pilot Dan Web airlaid forming equipment by depositing the following layers:
Layer 1: Blend of 10 gsm polyester fiber, Kosa, merge #35379A, 6.7 dtex, 4 mm, and 20 gsm bicomponent AL Delta binder fiber, 6.7 dtex, 6 mm, from FiberVisions a/s, Varde, Denmark.
Layer 2: Blend of 40 gsm cellulose fiber, FOLEY FLUFFS® and 10 gsm Trevira bicomponent binder fiber, merge #1663, 2.0 dtex, 3 mm, from Trevira Neckelmann a/s, Silkeborg, Denmark.
Layer 3: Blend of 41.5 gsm cellulose fluff, FOLEY FLUFFS® and 4.0 gsm Trevira bicomponent binder fiber, merge #1663.

Liquid binder AF-192 (Air Products) was sprayed at 10% solids on the surface of Layer 3 in an amount of 1.5 gsm based on the dry solids weight. The sheets were pressed slightly and cured in the lab convection oven at 150° C. for 15 minutes. The density of the sheets was 0.035 g/cm$^3$.

Figure 7:
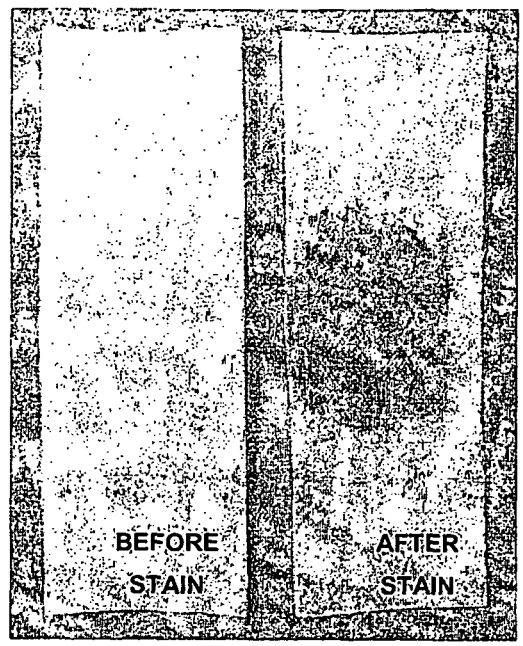
FIG. 7 illustrates the top surface of a sheet before and after a colored liquid was applied on its surface. The figure shows the masking effect produced by the treatment of the sheet.

A foam was prepared with Tylac-NW-4036-51B latex (Reichhold) at 15% solids by weighing 84.6 g latex (53% solids) and diluting it with 300 g and beating the mixture in a cake mixer on maximum speed for 3 minutes. A small handsheet was cut out of Web #7. The surface of Layer 1 was subsequently covered with a template with openings masking a part of the area to produce a "flower" pattern. Then the foam of Tylac-NW-4036-51B latex was spread evenly over the entire surface. The excess foam was removed by lightly scraping the surface with a spatula and the sample was placed in an oven at 145° C. for 15 minutes. After curing, a photograph was taken of the top surface of the sheet and then a colored liquid was applied on its surface. When the liquid was absorbed another photograph was taken to show the masking effect produced by the treatment of the sheet. The photographs are displayed in FIG. 7.

Example 10

Treating Handsheets

A 10% aqueous solution of sodium oleate was sprayed onto one half of the front of a 5"×8" piece of SW-16 pulp sheet, lot #625649, available from Buckeye Technologies Inc. The sheet was placed in a drying oven at 70° C. for 15 minutes. After the pulp sheet cooled to ambient temperature, a drop of water was placed on the untreated half of the pulp sheet. It immediately soaked into the pulp sheet. A drop of water placed on the treated half of the pulp sheet remained on the surface with a very high contact angle.

Example 11

Using the laboratory airlaid forming device homogeneous sheets were prepared, each having a basis weight of 150 gsm. The composition and thickness of each sheet is shown in Table 3. The sheets containing bicomponent binder fibers were cured in a laboratory convection oven at 150° C. The times of curing are given in Table 3. The sheets were then tested for permeability of defibrinated sheep blood. Each sheet was placed on a beaker so that the liquid could penetrate through it and drop into the beaker. The defibrinated sheep blood in an amount of 6 mL was poured from a narrow cylinder onto the top of each sheet and the time was measured from the moment the whole amount of blood was deposited on the sheet until the moment the liquid started to drop into the beaker from the bottom side of the sheet. This time was called strike-through time and is recorded in Table 3. After the whole amount of blood passed through the sheet the diameter of the stain on the top side of the sheet was measured and the results are contained in Table 3. Based on the data given in Table 3 the conclusion can be drawn that the sheets made with CARESSA 3100® fibers and bonded with bicomponent fiber had a higher permeability than the unbonded sheets and the bonded sheets made with FOLLY FLUFFS® and bicomponent fibers. It is thought that this effect was due to the fact that the bicomponent fiber contained a fatty-acid based finish which reacted with the Al ions on the CARESSA 3100® fibers. As a result of this reaction the stability of the bonded web comprising CARESSA 3100® fibers was enhanced due to additional inter-fiber bonds thus preventing it from collapsing. Another aspect of the fatty-acid metal ion interaction is that the reaction between the finish on the bicomponent fibers and the Al ions on the CARESSA 3100® fibers lowered the surface energy of the fibers. This in turn inhibited the wicking of the liquid in the planar direction within the web and resulted in a small stain size.

TABLE 3

| Sheet composition | Thickness, mm | Curing time, minutes | Strike-through time, seconds | Top stain diameter, mm |
|---|---|---|---|---|
| FF*) | 1.40 | 0 | 54.7 | 80 |
| SW-25**) | 1.42 | 0 | 61.0 | 90 |
| FF 75%/Bico***) 25% | 1.87 | 0 | 85.2 | 60 |
| FF 75%/Bico 25% | 1.88 | 5.0 | 86.2 | 90 |
| SW-25 75%/Bico 25% | 1.83 | 1.5 | 20.3 | 30 |
| SW-25 75%/Bico 25% | 1.83 | 4.0 | 26.4 | 30 |

*)FF—FOLLY FLUFFS ®
**)SW-25 - CARESSA 3100 ®
***)Bico—Trevira bicomponent fiber Example 12

Testing Tensile Strength

Using the laboratory airlaid forming device homogeneous sheets were prepared, each having a basis weight of 100 gsm and a density of 0.045 g/cm$^3$. The composition of each sheet is shown in Table 4. The sheets containing bicomponent binder fibers were cured in a laboratory convection oven at 150° C. for the times given in Table 4. The sheets, each 2.5 cm wide and 10 cm long, were then tested for tensile strength and the results are recorded in Table 4. These results suggest that the amount of curing time necessary to obtain the maximum tensile strength is significantly less in the case of the webs comprising the SW-16 fibers than in the case of the webs which do not contain these fibers. One can postulate that the curing process provides conditions for rapid creation of additional bonds between the fibers in the web. It is quite likely that this effect is associated with the interaction between the Al ions on the SW-16 fibers and the fatty-acid containing finish on the bicomponent fibers. As a result, not only the time of curing can be reduced but the tensile strength is higher than that of the webs which do not comprise fibers with Al ions.

TABLE 4

| | Tensile strength, N, after curing for | | |
|---|---|---|---|
| Sheet composition | 3 min | 7 min | 10 min |
| SW-16 95%/Bico*) 5% | 0.8 | 1.3 | 1.3 |
| SW-16 90%/Bico 10% | 2.7 | 3.8 | 3.3 |
| SW-16 85%/Bico 15% | 7.2 | 6.5 | 5.5 |
| FF**) 95%/Bico 5% | 0.3 | 0.8 | 1.0 |
| FF 90%/Bico 10% | 0.4 | 2.8 | 3.1 |
| FF 85%/Bico 15% | 0.8 | 5.0 | 5.3 |

*)Bico—bicomponent fiber
**)FF—FOLLY FLUFFS ®

Example 13

Testing Tensile Properties 50 grams of sodium oleate flake from Norman, Fox & Co. was mixed with distilled water to form a 10% sodium oleate solution with stirring and heating to completely dissolve the flake. The 10% solution was sprayed at a loading 1.0 part of sodium oleate per 100 parts of fiber onto one surface of a sheet of CARESSA® 1100 fiber, obtained from Buckeye Technologies Inc., which had an aluminum content of 7,685 ppm and a citric acid content of 4.5%. Sheets were also prepared with loadings of 0.5 part per 100 parts of fiber and 0.25 part per 100 parts of fiber.

The 10% sodium oleate solution was sprayed at a loading 1.0 part of sodium oleate per 100 parts of fiber onto one surface of a sheet of Foley Fluffs®, obtained from Buckeye Technologies Inc. Sheets were also prepared with loadings of 0.5 part per 100 parts of fiber and 0.25 part per 100 parts of fiber.

The 10% sodium oleate solution was sprayed at a loading 1.0 part of sodium oleate per 100 parts of fiber onto one surface of a sheet of Foley Fluffs® containing precipitated aluminum, obtained from Buckeye Technologies Inc., which had an aluminum content of 7,827 ppm. Sheets were also prepared with loadings of 0.5 part per 100 parts of fiber and 0.25 part per 100 parts of fiber.

The pulp sheets were allowed to air-dry overnight at a room temperature of 22° C. Handsheets were made from each fiber according to TAPPI Method T205 except that a 0.5% consistency slurry was used during the disintegration step and the handsheets were not pressed.

The following properties were measured on the unpressed TAPPI handsheets: permeability (cfm/ft.$^2$), dry tensile (g/in), bulk (cc/g), initial wet tensile (g/in) and 5-minute wet tensile (g/in). Permeability was determined using an air permeability tester. Specifically, four handsheets per experimental fiber were tested in the air permeability tester. For each handsheet a pressure drop of one half inches of water was established across the handsheet and air flow through the sheet was measured by the pressure drop across an orifice indicated on a vertical manometer. The average manometer reading was converted to air permeability using conversion tables. This method is described in U.S. Pat. No. 6,171,441 which is hereby incorporated by reference herein in its entirety. Dry tensile values were determined using TAPPI Method T494. Wet tensile values were determined using TAPPI Method T456, pre-1997 edition.

The results in Tables 5 and 6 showed that adding sodium oleate to the fibers did not significantly impact permeability, dry tensile or bulk. The wet tensile strength showed an increase when sodium oleate was added to fibers containing aluminum. The following graph depicts the interaction between sodium oleate and aluminum containing fibers.

TABLE 5

Wet Tensile Data (g/in)

| Fiber | Sodium Oleate Add-on | | | |
|---|---|---|---|---|
|  | 0% | 0.25% | 0.50% | 1.00% |
| Foley Fluffs ® | 13 | 18 | 19 | 13 |
| Caressa 1100 | 28 | 168 | 244 | 261 |
| Foley Fluffs ® with Aluminum | 54 | 32 | 233 | 270 |

TABLE 6

Contact Angle Data

| Fiber | Sodium Oleate Add-on | | | |
|---|---|---|---|---|
|  | 0% | 0.25% | 0.50% | 1.00% |
| Foley Fluffs ® | 27.0 | 24.0 | 21.2 | 41.1 |
| Caressa 1100 | Too fast | 97.5 | 113.4 | 118.8 |
| Foley Fluffs ® with Aluminum | Too fast | 92.4 | 101.6 | 105.6 |

Example 14

Cellulose fibers were treated as follows. A total of 9.36 parts hydrated aluminum sulfate $(Al_2(SO_4)_3*14H_2O)$ from General Chemical Corporation, per 100 parts bleached southern softwood Kraft (13SSK) fibers from Buckeye Technologies were added to a slurry consisting of 4.5 parts fiber/100 parts slurry. The slurry had a pH of 3.2. After 25 minutes of mixing 3.0 parts sodium hydroxide/100 parts fiber were added along with sufficient water to provide 0.9 parts fiber/100 parts slurry at a pH of 5.7. The temperature was adjusted to 60° C. The resultant slurry was continuously dewatered on a sheeting machine where the sheet was formed at 1.0 rush/drag ratio, couched, then pressed and densified using three stages of pressing to 48 parts fiber/100 parts total. The sheet was dried using conventional drum dryers to 93.5 percent solids. While continuously reeling, a spray of heated 10% aqueous sodium oleate (from Norman, Fox & Co.) solution was applied to one surface of the sheet at a loading of 1.0 part per 100 parts of fiber. The reeled sheet was then sized into individual rolls. The fiber was found to be hydrophobic and exhibited significant wet strength.

Example 15

A slurry of bleached southern softwood Kraft (BSSK) fibers from Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine and a sheet was formed at a rush/drag ratio of 1.0, couched, then pressed and densified through three stages of pressing to 48 parts fiber/100 parts slurry. The sheet was dried using conventional drum dryers to 93.5 percent solids. The sheet was then reeled. During reeling, 6.1 parts of hydrated aluminum sulfate $(Al_2(SO_4)_3*14H_2O$, 50% aqueous solution) and 1.0 part of heated sodium oleate (10% aqueous solution) are applied by spraying per 100 parts. The fiber was reeled on a continuous roll. The reeled sheet was then sized into individual rolls. The sheet became hydrophobic after treatment.

Example 16

Cellulose fibers were treated as follows. A total of 9.36 parts hydrated aluminum sulfate $(Al_2(SO_4)_3*14H_2O)$ from General Chemical Corporation and 3 parts of (10% aqueous sodium oleate) solution per 100 parts bleached southern softwood Kraft (BSSK) fibers from Buckeye Technologies were added to a slurry consisting of 4.5 parts fiber/100 parts slurry. The slurry had a pH of 3.2. After 25 minutes of mixing 3.0 parts sodium hydroxide/100 parts fiber were added along with sufficient water to provide 0.9 parts fiber/100 parts slurry at a pH of 5.7. The temperature was adjusted to 60° C. The resultant slurry was continuously dewatered on a sheeting machine where the sheet was formed at 1.0 rush/drag ratio, couched, then pressed and densified using three stages of pressing to 48 parts fiber/100 parts total. The sheet was dried using conventional drum dryers to 93.5 percent solids. The reeled sheet was then sized into individual rolls. As a result of this treatment, the paper became hydrophobic.

Example 17

12.1 g of ferric nitrate $(Fe(NO_3)_3)$ Fisher Chemical Co.) per 152 g bleached southern softwood Kraft (BSSK) fibers from Buckeye Technologies were added to a slurry of 4.5 parts fiber/100 parts slurry. The slurry had a pH of 2.76. After mixing and dilution to 0.9 parts fiber/100 parts slurry, 27.1 ml of 10% sodium hydroxide were added to provide a pH of 5.7. The resultant slurry was dewatered on a dynamic handsheet former (Formette Dynamique Brevet, Centre Technique de L'Industrie, Ateliers de Construction Allimand, Appareil No. 48) and was pressed to 48 parts fiber/100 parts total. The sheet was dried to 93.5 percent solids. After drying, 1 part of 10% aqueous sodium oleate solution per 100 parts of fiber was applied to the sheet.

Example 18

9.36 parts hydrated aluminum sulfate $(Al_2(SO_4)_3*14H_2O)$ per 100 parts bleached southern softwood Kraft (BSSK) fibers from Buckeye Technologies were added to a slurry consisting of 4.5 parts fiber/100 parts slurry. After addition of the aluminum sulfate, the slurry had a pH of 3.2. After 25 minutes of mixing, 3.0 parts sodium hydroxide/100 parts fiber were added along with sufficient water to provide 0.9 parts fiber/100 parts slurry at a pH of 5.7 and temperature of 60° C. The resultant slurry was continuously dewatered on a sheeting machine and a sheet formed at a 1.0 rush/drag ratio, couched, then pressed and densified using three stages of pressing to 48 parts fiber/100 parts total. A spray of heated 10% aqueous sodium oleate solution was applied to one surface of the sheet at a loading of 1.0 part per 100 parts of fiber. The sheet was dried to 93.5 percent solids. As a result of this treatment, the paper became hydrophobic.

Example 19

High porosity commercial fiber (HPZ) was obtained from Buckeye Technologies Inc. in sheet form. The fibers had a WRV of 78.3, a curl of 51% and a 97.9% alpha cellulose content. A total of 9.36 parts of aluminum sulfate ($Al_2(SO_4)_3*14H_2O$) per 100 parts fiber were added to a slurry of 4.5 parts fiber/100 parts slurry. The slurry had a pH of 3.2. After 25 minutes of mixing, 3.0 parts sodium hydroxide/100 parts fiber were added along with sufficient water to provide 0.9 parts fiber/100 parts slurry at a pH of 5.7. The resultant slurry was dewatered on a dynamic handsheet former (Formette Dynamique Brevet, Centre Technique de L'Industrie, Ateliers de Construction Allimand, Appareil No. 48) and was pressed to 48 parts fiber/100 parts total. The sheet was dried to 93.5 percent solids. After drying, 1.0 part of heated sodium oleate (Norman, Fox & Co.) per 100 parts fiber were applied to the sheeted material by spraying.

Example 20

High purity commercial cotton fiber (GR512) was obtained from Buckeye Technologies Inc. in sheet form. A total of 7.7 parts of aluminum sulfate ($Al_2(SO_4)_3*14H_2O$) per 100 parts fiber were added to a slurry of 4.5 parts fiber/100 parts slurry. The slurry had a pH of 3.2. After 25 minutes of mixing, 3.0 parts sodium hydroxide/100 parts fiber were added along with sufficient water to provide 0.9 parts fiber/100 parts slurry at a pH of 5.7. The resultant slurry was dewatered on a dynamic handsheet former (Formette Dynamique Brevet, Centre Technique de L'Industrie, Ateliers de Construction Allimand, Appareil No. 48) and was pressed to 48 parts fiber/100 parts total. The sheet was dried to 93.5 percent solids. After drying, 1.0 part of sodium oleate (Norman, Fox & Co.) per 100 parts fiber were applied to the sheeted material by spraying. The sheet was found to be hydrophobic and exhibited wet strength.

Example 21

A slurry of bleached southern softwood Kraft (BSSK) fibers Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine where the sheet was formed at a rush/drag ratio of 1.0, couched, then treated by spraying with 12.35 parts of hydrated aluminum sulfate and 3.17 parts of sodium hypophosphite per one hundred parts of fiber, then pressed and densified through three stages of pressing to 48 parts fiber/100 parts slurry. The sheet was dried using conventional drum dryers to 93.5 percent solids. After drying, 1 part of 10% aqueous sodium oleate solution per 100 parts of fiber was applied to the sheet. The fiber was reeled on a continuous roll. The resultant reel was sized into individual rolls.

Example 22

A slurry of bleached southern softwood Kraft (BSSK) fibers Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine where the sheet was formed at a rush/drag ratio of 1.0, couched, then treated by spraying with 12.35 parts of hydrated aluminum sulfate, 1.0 part of sodium oleate and 3.17 parts of sodium hypophosphite per one hundred parts of fiber, then pressed and densified through three stages of pressing to 48 parts fiber/100 parts slurry. The sheet was dried using conventional drum dryers to 93.5 percent solids. The fiber was reeled on a continuous roll. The resultant reel was sized into individual rolls.

Example 23

A total of 9.36 parts of hydrated aluminum sulfate ($Al_2(SO_4)_3*14H_2O$) per 100 parts of bleached southern softwood Kraft (BSSK) fibers from Buckeye Technologies were added to a slurry consisting of 4.5 parts fiber/100 parts slurry. The slurry had a pH of 3.2. After 25 minutes of mixing, 3.0 parts of sodium hydroxide per 100 parts of fiber were added with sufficient water to provide 0.9 parts fiber per 100 parts slurry at a pH of 5.7 and at a temperature of 60° C. The resultant slurry was continuously dewatered on a sheeting machine where the sheet was formed at a rush/drag ratio of 1.0, couched, then treated by spraying with 12.35 parts of hydrated aluminum sulfate and 3.17 parts of sodium hypophosphite per one hundred parts of fiber, then pressed and densified through three stages of pressing to 48 parts fiber/100 parts slurry. The sheet was dried using conventional drum dryers to 93.5 percent solids. After drying, 1 part of 10% aqueous sodium oleate solution per 100 parts of fiber was applied to the sheet. The fiber was reeled on a continuous roll. The resultant reel was sized into individual rolls.

Example 24

A slurry of bleached southern softwood Kraft (BSSK) fibers Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine where the sheet was formed at a rush/drag ratio of 1.0, couched, then pressed and densified through three stages of pressing to 48 parts fiber/100 parts slurry, then treated by spraying with 12.35 parts of hydrated aluminum sulfate, 1.0 part of sodium oleate and 3.17 parts of sodium hypophosphite per one hundred parts of fiber. The sheet was dried using conventional drum dryers to 93.5 percent solids. The fiber was reeled on a continuous roll. The resultant reel was sized into individual rolls.

TABLE 7

Contact Angle Data - Different Add-on Techniques - Dynamic Handsheet

| Fiber | Sodium Oleate Add-on | | | |
|---|---|---|---|---|
| | 0% | 0.75% | 1.50% | 3.00% |
| Foley Fluffs ® Fatty Acid co-precipitated with Aluminum | Too Fast | 72.9 | 94.2 | 102.6 |
| Foley Fluffs ® with Aluminum Fatty Acid sprayed on prior to drying | Too fast | 100.0 | 107.8 | 116.6 |

TABLE 7-continued

Contact Angle Data - Different Add-on Techniques - Dynamic Handsheet

| | | | | |
|---|---|---|---|---|
| Foley Fluffs ® with Aluminum Fatty Acid sprayed on after drying | Too fast | 91.0 | 98.2 | 110.2 |
| Fiber | | 0% | 1.50% | 3.00% |
| Sodium Oleate Add-on (5,000 ppm of Aluminum) - Dynamic Handsheets | | | | |
| Foley Fluffs ® Co-precipitated | | — | 176 | 168 |
| Foley Fluffs ® with Aluminum Fatty Acid added before drying | | 42 | 245 | 279 |
| Foley Fluffs ® with Aluminum Fatty Acid added after drying | | 42 | 189 | 220 |
| Sodium Oleate Add-on (10,000 ppm of Aluminum) - Dynamic Handsheets | | | | |
| Foley Fluffs ® Co-precipitated | | — | 30 | 112 |
| Foley Fluffs ® with Aluminum Fatty Acid added before drying | | 37 | 98 | 197 |
| Foley Fluffs ® with Aluminum Fatty Acid added after drying | | 37 | 111 | 205 |

Description of Organic Acids Bound to Fibers by Organic Cations

Long chain saturated or unsaturated organic acids may be bound to cellulose fibers by precipitation or insolubilization with polyvalent metal cations as described above. Similarly, long chain saturated or unsaturated organic acids may be bound to cellulose fibers by precipitation or insolubilization with polyvalent organic cations. Examples of such organic cations are cationic starches, cationic polyacrylamides or polydiallyldimethyl ammonium chlorides. Cationic starches useful in the practice of this invention include the Redibond® family of dry strength polymers from National Starch & Chemical Company. Cationic polyacrylamides useful in the practice of this invention include Baystrength™ dry strength polymers from Bayer Chemical Company. Polydiallyldimethyl ammonium chlorides useful in the practice of this invention include polydiallyldimethyl ammonium chlorides from Aldrich Chemical Company.

In general, the polyvalent organic cation must be soluble in water and form an insoluble product when mixed with the anion of an organic acid. This insoluble product will be retained on a surface such as that of a cellulose fiber, when the two chemicals are combined in an aqueous mixture of the fibers.

Example 25

Cellulose fibers in an aqueous slurry with a solids content of from 1 to 3 percent solids content are adjusted to pH of about 7 to 8, to maximize the anionic content of the fibers. A polyvalent organic cationic having cationic content in excess of the anionic content of the fibers and approximately 0.5 weight percent based on the dry weight of the fibers is dissolved in water at the same pH as the fiber slurry and mixed with the fiber slurry. After 30 minutes the maximum retention of polyvalent organic cation is achieved, converting the fibers to an overall cationic surface. A solution of the long chain organic acid in anionic form, for example, the sodium salt, at the same pH as the fiber slurry is mixed with the fiber slurry. After 30 minutes, the maximum retention of organic acid anion to the cationized fibers is achieved. The fibers are drained, washed, made into TAPPI handsheets and the contact angle is then determined.

Example 26

Cellulose fibers in an aqueous slurry with a solids content of from 1 to 3 percent solids content were adjusted to pH of about 7 to 8. A cationic starch from the Redibond® product line, approximately 0.5 weight percent based on the dry weight of the fibers, was dissolved in water at the same pH as the fiber slurry and mixed with the fiber slurry. After 30 minutes an aqueous solution of sodium laurate, approximately 0.1 weight percent based on the dry weight of the fibers, at the same pH as the fiber slurry was mixed with the fiber slurry. After 30 minutes, the fibers were drained, washed, made into TAPPI handsheets and the contact angle was measured.

Example 27

A mixture of cellulose fibers in an aqueous slurry (1-3% solids content) and 0.1% weight percent based on dry fiber weight of sodium laurate were mixed and the pH adjusted to 7-8. A cationic starch from the Redibond® product line, 0.5 weight percent based on dry fiber weight, was dissolved in water at the same pH as the fiber slurry and the solution added to the fiber sodium laurate mixture. After 30 minutes of mixing, the fibers were drained, washed, made into TAPPI handsheets and the contact angle measured.

Example 28

Cellulose fibers in an aqueous slurry (1-3% solids content) were adjusted to pH 7-8, to maximize the anionic content of the fibers. A cationic starch from the Redibond® product line, 0.5 weight percent based on dry fiber weight, was dissolved in water at the same pH as the fiber slurry and mixed with the fiber slurry. After 30 minutes of mixing, the fibers were drained washed and made into TAPPI handsheets. An aqueous solution of sodium laurate, 0.1 weight percent based on the dry weight of the fibers, at the same pH as the fiber slurry was sprayed onto handsheets made from the fiber cationic starch mixture. After one hour at ambient temperature, the sheets were dried to constant weight at 50° C. The treated handsheets were then slurried in water at pH 7-8, the fibers were formed into TAPPI handsheets and the contact angles were measured.

Example 29

Cellulose fibers in an aqueous slurry (1-3% solids content) were adjusted to pH 7-8, to maximize the anionic content of the fibers. A cationic polydiallydimethyl ammonium chloride, 0.5 weight percent based on dry fiber weight, was dissolved in water at the same pH as the fiber slurry and mixed with the fiber slurry. After 30 minutes of mixing, the fibers were drained washed and made into TAPPI handsheets. An aqueous solution of sodium laurate, 0.1 weight percent based on the dry weight of the fibers, at the same pH as the fiber slurry was sprayed onto handsheets made from the fiber cationic starch mixture. After one hour at ambient temperature, the sheets were dried to constant weight at 50° C. The treated handsheets were then slurried in water at pH 7-8, the fibers were formed into TAPPI handsheets and the contact angles were measured.

Example 30

Vapor Phase Application

Dry cellulose fibers containing aluminum hydroxide are exposed to the vapor of molten oleic acid (stearic acid) for one hour. The vapor phase organic acid is bound to the aluminum on the fibers, and the fibers are formed into a handsheet. The contact angel of the produced fibers is then determined.

Example 31

Medium Consistency Application

An aqueous slurry of aluminum hydroxide containing cellulose fibers (10% solids content) is mixed with an aqueous solution of sodium oleate (1 wt. % on dry fiber basis) in a medium consistency high shear mixer, for 15 seconds. The mixture is heated for one hour at 50° C., with 5 seconds of mixing every 15 minutes. The fibers are removed from the mixer and washed well with hot water. The fibers are formed into a handsheet, and the contact angle is then determined.

Example 32

Medium Consistency Application

An aqueous slurry of cellulose fibers (10% solids content) is mixed with 1 wt. % (dry fiber basis) of aluminum sulfate octadecahydrate and placed in a medium consistency high shear mixer. Then, an aqueous solution of sodium oleate (1 wt. % on dry fiber basis) is mixed with the fiber slurry in medium consistency high shear mixer, for 15 seconds. The mixture is heated for one hour at 50° C., with 5 seconds of mixing every 15 minutes. The fibers are removed from the mixer washed well with hot water. The fibers are formed into a handsheet, and the contact angle is then determined.

Example 33

Medium Consistency Application

An aqueous slurry of cellulose fibers (10% solids content) is mixed with 1 wt. % (dry fiber basis) of calcium chloride and placed in a medium consistency high shear mixer. Then an aqueous solution of sodium oleate (1 wt. % on dry fiber basis) is mixed with the fiber slurry in medium consistency high shear mixer, for 15 seconds. The mixture is heated for one hour at 50° C., with 5 seconds of mixing every 15 minutes. The fibers are removed from the mixer and washed well with hot water. The fibers are formed into a handsheet, and the contact angle is then determined.

Example 34

Medium Consistency Application

An aqueous slurry of cellulose fibers (10% solids content) is mixed with an aqueous solution of sodium oleate (1 wt. % on dry fiber basis) in a medium consistency high shear mixer, for 15 seconds. Then, an aqueous solution of aluminum sulfate octadecahydrate (or calcium chloride) 1 wt. % on dry fiber basis is mixed with the fiber slurry in a medium consistency high shear mixer for 15 seconds. The mixture is heated for one hour at 50° C., with 5 seconds of mixing every 15 minutes. The fibers are removed from the mixer and washed well with hot water. The fibers are formed into a handsheet, and the contact angle is determined.

Examples 35 through 41 below further illustrate the invention, and, as used therein, "% weight/volume" is used to describe the concentration of a given compound in grams per 100 mL of solvent. So, instead of saying "0.2% (weight/volume) solution of stearic acid in chloroform" we can say "solution of stearic acid in chloroform having concentration of 0.2 g stearic acid per 100 ml chloroform.

Example 35

A rectangular, 10 cm by 10 cm sample of wet laid paper having basis weight of about 100 gsm was made with Buckeye FFLE+™ pulp. The sheet was impregnated with 1 ml of a 0.2% (weight/volume) solution of stearic acid in chloroform. After evaporating the chloroform under the hood, the sheet was placed above a sintered glass under which a slight vacuum was maintained and a stream of air at 80-100° C. was passed by means of a laboratory hair drier through the sheet for a few seconds. As a result of this treatment the paper became hydrophobic.

Example 36

The treatment was performed according to the invention on hydrophilic cotton, sawdust, a piece of board, a cellulose acetate filter and Cellophane with stearic acid solution in chloroform in a stream of hot air coming from a hair drier as indicated in previous examples. All these materials became hydrophobic after treatment.

Example 37

A 1% (weight/volume) solution of perfluorooctanoic acid was prepared in chloroform, a piece paper made with Buckeye FFLE+™ cellulose was soaked quickly in it. Then the solvent was evaporated and the paper was subjected to a stream of hot air at 140° C. for few seconds. The sample thus prepared was then tested for its oleophobic character by depositing a drop of vegetable oil on the surface. It was found that the oil remained on the surface of the paper without wetting it.

Example 38

A dual-flow spray nozzle was used, fed with stearic acid heated above its boiling point chloride at a liquid flow rate of 0.6 ml/min. A piece of rectangular, 10 cm by 10 cm paper made with Buckeye FFLE+™ cellulose was placed under the nozzle at a distance of 10 cm for a period of one second so that a quantity of about 10 mg was deposited on the paper. The paper was then placed in an oven for 15 seconds. The paper became hydrophobic.

Example 39

A rectangular, 10 cm by 10 cm sample of wet laid paper having basis weight of about 100 gsm was made with Buckeye FFLE+™ pulp. The sheet was impregnated with 1 ml of a 0.2% (weight/volume) solution of sodium oleate in water. The sheet was placed above a sintered glass under which a slight vacuum was maintained and a stream of air at 80-100°

C. was passed by means of a laboratory hair drier through the sheet until the sheet was dry. As a result of this treatment the paper became hydrophobic.

Example 40

A sample of air laid paper having basis weight of about 100 gsm was made on a lab sheet forming equipment using 90 gsm Buckeye FFLE+™. The sheet was sprayed on one side with 5 gsm based on the dry weight of binder (AF192, Air Products), cured at 140° C. for 10 minutes and then sprayed on the other side with 5 gsm based on dry weight of the same binder and cured again in the same conditions. The produced sheet was hydrophilic. A rectangular, 10 cm by 10 cm sample of the sheet was then sprayed with a microdispersion of 1 ml of a 0.2% (weight/volume) solution of sodium oleate in water. The sheet was placed above a sintered glass under which a slight vacuum was maintained and a stream of air at 80-100° C. was passed by means of a laboratory hair drier through the sheet until the sheet was dry. As a result of this treatment the paper became hydrophobic.

Example 41

Southern softwood cellulose (FOLEY FLUFFS®, Buckeye) sheet was impregnated with stearic acid by treating it with a microdispersion of a 0.5% (weight/volume) solution of stearic acid in chlorphorm. The sheet was then dried under the hood and disintegrated into fluff on a lab equipment.

A sample of air laid paper having basis weight of about 100 gsm was made on a lab sheet forming equipment using 47.5 gsm of the cellulose containing stearic acid, 47.5 gsm FFLE+™ and 5 gsm Trevira #1663 bicomponent binder fiber. The airlaid sheet was cured at 140° C. for 10 minutes by applying a stream of hot air. As a result of this treatment the whole sheet became hydrophobic.

Example 42

Measurement of Water Retention Value

One gram cellulose of known water content was disintegrated, put into a 200 ml Erlenmayer flask and suspended in 100 ml distilled water. The suspension was agitated for 1 h at 20° C., then transferred to a G3 sintered-glass disk to remove the excess water under reduced pressure. The sintered-glass disk was then transferred to a centrifuge tube and centrifuged at 2000 G for 15 minutes. Subsequently the weight of the moist sample was determined. The water retention value was calculated according to the formula:

$$WRV(\%) = \frac{\left(\frac{\text{Mass of moist sample} - }{\text{Mass of dry sample}}\right) \times 100}{\text{Mass of dry sample}}$$

Three WRV measurements were taken for each fiber sample to get an average value.

Example 43

Measurement of Contact Angle

Figure 11:
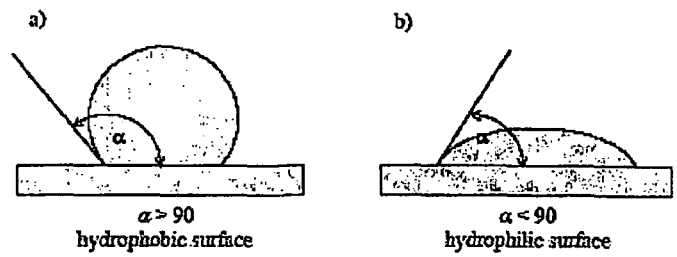
FIG. 11 shows the contact angle between a water droplet meniscus and the surface of the cellulose sheet.

The hydrophobicity of cellulose is determined by measuring the contact angle between the water droplet meniscus and the surface of the cellulose sheet. The surface becomes hydrophobic, when the contact angle α exceeds 90° as illustrated in FIG. 11.

Contact angle measurements were done with Pocket Goniometer PG-1, according to ASTM D724 (Standard Test Method for Surface Wettability of Paper). A drop (0.5 µl) of the test liquid (demineralized water) was placed on the surface of the tested handsheet. The resultant contact angle was measured from the optical micrograph of the drop. Seventy measurements were done for each sample. The average contact angle and standard deviation were calculated in each case.

Example 44

Preparation of Sodium Salts of Fatty Acids

Sodium hydroxide solution was prepared by addition of 6 moles NaOH (240 g) to the mixture of 800 mL methanol and 200 mL water.

One gram of a fatty acid chosen from the list of fatty acids in Table 8 was dissolved in 50 mL methanol. If the fatty acid was insoluble at ambient temperature, the temperature of the mixture had to be raised until a solution could be obtained.

TABLE 8

| Name | General Formula | Structural Formula |
| --- | --- | --- |
| Lauric acid | $C_{12}H_{24}O_2$ | |
| Myristic acid | $C_{14}H_{28}O_2$ | |
| Palmitic acid | $C_{16}H_{32}O_2$ | |
| Palmitoleic acid | $C_{16}H_{30}O_2$ | |

TABLE 8-continued

| Name | General Formula | Structural Formula |
|---|---|---|
| Stearic acid | $C_{18}H_{36}O_2$ | CH3-(CH2)16-COOH |
| Oleic acid | $C_{18}H_{34}O_2$ | CH3-(CH2)7-CH=CH-(CH2)7-COOH |
| Linoleic acid | $C_{18}H_{30}O_2$ | CH3-(CH2)4-CH=CH-CH2-CH=CH-(CH2)7-COOH |
| Ricinoleic acid | $C_{18}H_{33}O_3$ | CH3-(CH2)5-CH(OH)-CH2-CH=CH-(CH2)7-COOH |

The prepared solution of the fatty acid was then added to the molar equivalent of sodium hydroxide dissolved previously in the methanol/water mixture. As a result the obtained product was sodium salt of the fatty acid, which will be called here also as "sodium soap". Subsequent to that water was added to obtain a total of 1000 mL of the sodium soap solution.

As an example the following procedure was used to obtain a solution of sodium stearate:

Take 1 g stearic acid (0.0035 mol), dissolve in 50 ml methanol at 60° C. Add 0.0035 mol NaOH/methanol solution (21.1 ml of prepared solution), and sufficient volume of water to obtain 1000 ml.

In addition to the sodium salts prepared in the above manner, a commercial sodium soap was used composed mainly of sodium oleate. This chemical was supplied by Valley Products (Memphis, Tenn.). Its commercial name is "Val Pro GM". The name which is used in the following examples is also "Valpro".

Example 45

Deposition of Aluminum Hydroxide on Cellulosic Fibers

Never-dried pulp (152 g by bone-dry weight) was added to 6 liters soft water and agitated to obtain a slurry at cellulose consistency of about 2.5%. Then an aqueous solution of sulfuric acid having a concentration of 10% by weight was slowly added to the pulp slurry until the pH was in the range of 3.6 to 4.0. 5. After that appropriate amount of hydrated aluminum sulfate $Al_2(SO_4)_3.18H_2O$ was introduced to the 6-liter slurry, depending on the targeted content of Al in cellulose. The amounts of $Al_2(SO_4)_3.18H_2O$ and the target contents of Al in the prepared cellulose pulp batches are given in Table 9.

The mixture was agitated for about 15 minutes. In the meantime 13 liters of demineralized water placed in a separate bucket and the pH adjusted to 3.5-3.7, using an aqueous solution of sulfuric acid at a concentration of 10% by weight. The 6 liter slurry of fiber with $Al_2(SO_4)_3.18H_2O$ was then transferred to the bucket with 13 liters of water adjusted to pH 35-3.7. The resultant slurry was adjusted to pH 3.5 using again the 10% sulfuric acid solution. Then add, with agitation for about 15 minutes, an aqueous solution of sodium hydroxide at a concentration of 10% by weight to bring the pH up to 5.7+/−0.2.

TABLE 9

| Amount of $Al_2(SO_4)_3.18H_2O$ added, grams | Target content of Al in cellulose, ppm |
|---|---|
| 0.94 | 500 |
| 1.87 | 1000 |
| 3.74 | 2000 |
| 5.62 | 3000 |
| 7.50 | 4000 |
| 9.37 | 5000 |
| 11.25 | 6000 |
| 14.06 | 7500 |
| 15.00 | 8000 |
| 18.75 | 10000 |

Example 46

Figure 12:
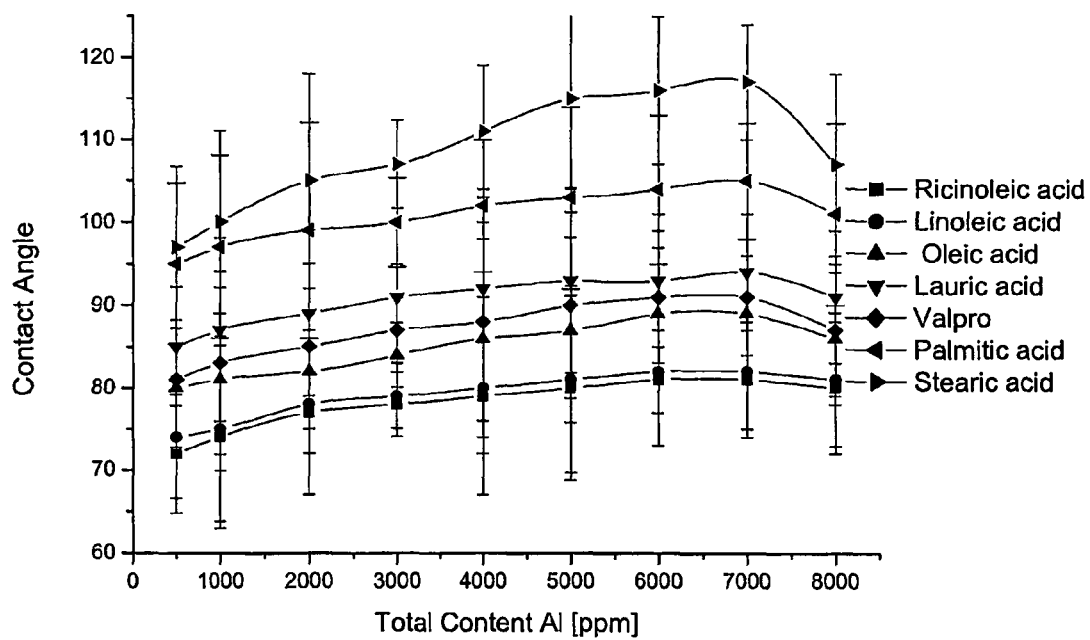
FIG. 12 shows the contact angle of various handsheets coated with soap solutions differing by acid type. The contact angle is shown over increasing aluminum content in ppm.

The Effect of Various Fatty Acids on the Hydrophobicity of the Treated Cellulose Handsheets with various aluminum contents were formed on laboratory equipment using the cellulose pulp samples prepared as described in Example 45. The handsheets were coated with various sodium soap solutions by spraying. The concentration of each soap solution was 1% and the resultant average soap add-on was 10 g/kg dry weight of cellulose. All sodium soap solutions were warmed to 70° C. to obtain homogenous liquids, and then were sprayed evenly on the surface of the handsheets. The coated handsheets were dried at 120° C. for 5 min. The time of drying was established for 5 min, as it was enough to obtain constant mass of the sample. The hydrophobicity of the dry handsheets was examined by contact angle measurements as described in Example 43. The results are illustrated in FIG. 12.

Example 47

Hydrophobic Cellulosic Fibers with Reduced Water Retention

Cellulose pulp (Buckeye Technologies Inc.) with aluminum content of 7000 ppm was prepared according to the lab procedure described in Example 45. Handsheets of basis weight approx. 300 g/m² were formed using lab forming equipment and then sprayed with citric acid solutions before drying. The concentrations of citric acid solutions were 1%, 4% and 10%. The citric acid add-on levels were, respectively: 4.3, 17.7 and 43.7 g per kg of cellulose. The handsheets were dried at 160° C. for 15 minutes and then sprayed with an aqueous solution of 1% sodium stearate by weight, preheated to 70° C. The add-on level of aluminum stearate was 10 g (dry weight) per kg cellulose. The samples were dried again at a temperature of 120° C. for 5 min to constant mass. Water retention value (WRV) was determined at each step of the process. The results of the WRV analyses are summarized in Table 10.

TABLE 10

| Amount of citric acid | | WRV of cellulose after spraying with citric acid and drying at 160° C., % | | Properties of cellulose after additional spraying with sodium stearate solution and drying, % | | |
|---|---|---|---|---|---|---|
| Concentration in application solution, % | Add-on, g/kg | Cellulose control (0 ppm Al) | Cellulose at 7000 ppm Al | WRV of cellulose control (0 ppm Al) | Cellulose at 7000 ppm Al WRV, % | Contact angle, deg |
| 0 | 0 | 98 | 93 | 93 | 82 | |
| 1 | 22 | 70 | 68 | 65 | 47 | 113 |
| 4 | 88 | 64 | 60 | 61 | 41 | 111 |
| 10 | 220 | 57 | 59 | 55 | 39 | 115 |

The following conclusions can be drawn from the data in Table 10:
WRV is practically not affected by the presence of Al in the fiber
The efficiency of the cross-linking reaction depends on citric acid add-on level. A decrease of WRV is observed with increased addition of citric acid.
A further decrease in WRV can be obtained as a result of the treatment of the cured cellulose with sodium stearate.

Example 48

Hydrophobic Cellulose Obtained by Pre-Swelling of the Fibers and Hydrophobic Treatment Cellulose in an amount of 2.5 g was added to 500 ml of 9% NaOH solution to make a slurry at consistency of 5%. After cooling the mixture to 15° C. aluminum sulfate in an amount of 6.14 g was added to achieve a target Al content in cellulose of 10000 ppm. Then an aqueous solution of sulfuric acid at a concentration of 10% by weight was added to adjust the pH to 5.7 and precipitate $Al(OH)_3$ within the swollen fibers. The excess amount of the liquid phase was removed (about ¾ of liquid volume) and 200 ml of 0.1% by weight of aqueous solution of stearic sodium soap was added. Then a handsheet (300 g/m²) was formed and dried it at 120° C. for 15 min. The WRV of the obtained sample was 49% and the contact angle was 103°. The sample was then disintegrated and rinsed with 10 liters distilled water (5 times by 2 liters of distilled water) and dried again at 120° C. for 15 min. The final WRV of thus prepared cellulose was 54% and the contact angle 101°.

Example 49

Hydrophobic Cellulose Obtained Using Zirconium Salt

A slurry was made using 152 g dry cellulose in 6 liters demineralized water. An aqueous solution of sulfuric acid at 10% by weight was then used to adjust the pH to 3.5-4.0. Subsequent to that 2.86 g $ZrOCl_2*8H_2O$ was added to the slurry to obtain the target content of Zr in cellulose at 5000 ppm. The slurry was agitated for about 15 minutes and transferred to a bucket with 13 liters demineralized water and the pH adjusted to 6.0-6.5 with an aqueous solution of sodium hydroxide at a concentration of 10% by weight. Thus obtained cellulose slurry was used to form handsheets having a basis weight of about 300 g/m². The sheets were dried at 120° C. and then coated with 1% by weight aqueous solution of sodium stearate previously warmed to 70° C. The add-on of the sodium soap on the sheet was at 10 g/kg cellulose. The contact angle of the treated sheet was 112°.

Example 50

Hydrophobic Cellulose Obtained by Direct Treatment with Aluminum Stearate

A cellulose sheet having a basis weight of about 300 g/m2 was coated with powdered aluminum stearate in an amount of 113.7 g per 1 kg cellulose to obtain a target content of Al in cellulose at 7000 ppm. The treated sheet was then cured in an oven at 130° C. for 5 minutes. The contact angle of the cured sheet was 121°.

Example 51

Treatment of Cellulose Containing Al with Stearic Acid on Synthetic Fiber Carrier A slurry of cellulose with deposited aluminum hydroxide was prepared as described in Example 45 to get a target Al content in cellulose at 7000 ppm. The slurry was vigorously agitated and polypropylene fibers cut to 3 mm were added to it in an amount of 3 g per 1 kg dry cellulose. The polypropylene fibers were made at Akademia Techniczno-Humanistyczna, Bielsko-Biala, Poland, and contained about 30% by weight of stearic acid. The obtained slurry of the blend of the cellulosic fibers with the polypropylene fibers was used to form handsheets on laboratory wet equipment and dried at 160° C. for 15 minutes. The contact angle of the cured sheet was 110°.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated by reference herein in their entireties for all purposes.

What is claimed is:

1. A fibrous material comprising a blend of fibers, wherein the blend of fibers comprises:
    (a) cellulosic fibers bound with a dissociating polyvalent cation-containing compound; wherein the polyvalent cation-containing compound is present in an amount from about 0.1 weight percent to about 20 weight percent based on the dry weight of the cellulosic fiber prior to treatment with the bound polyvalent cation-containing compound; and
    (b) synthetic fibers coated with a fatty acid containing compound, wherein substantially no polyvalent cation is present on the synthetic fibers; and
    wherein the fibrous material is hydrophobic.

2. The fibrous material of claim 1, wherein the fatty acid containing compound is selected from the group consisting of sodium oleate, methyl oleate, sodium laurate, oleic acid, stearic acid, and mixtures thereof.

3. The fibrous material of claim 1, wherein the polyvalent cation containing compound is a polyvalent metal ion salt.

4. The fibers of claim 3, wherein the polyvalent metal is selected from the group consisting of aluminum, iron, tin, and mixtures thereof.

5. The fibers of claim 4, wherein the polyvalent metal is aluminum.

6. The fibers of claim 3, wherein the polyvalent salt is selected from the group consisting of aluminum chloride, aluminum hydroxide, aluminum sulfate, and mixtures thereof.

7. The fibrous material of claim 1, wherein the contact angle of fibers in the blend of fibers is greater than 90°.

8. The fibrous material of claim 1, further comprising one or more fillers.

9. The fibrous material of claim 1, wherein the cellulosic fibers are cross linked and optionally treating the fibers with a cross-linking agent.

10. The fibrous material of claim 9, wherein the cross-linking agent is applied with thermal radiation.

* * * * *